United States Patent [19]
Rounbehler et al.

[11] Patent Number: 5,808,178
[45] Date of Patent: Sep. 15, 1998

[54] HIGH SPEED GAS CHROMATOGRAPHY

[75] Inventors: David P. Rounbehler, North Chelmsford; Eugene K. Achter, Lexington; David H. Fine, Lincoln; George B. Jarvis, Arlington, all of Mass.; Stephen J. MacDonald, Salem, N.H.; David B. Wheeler, Lunenburg; Clayton D. Wood, Framingham, both of Mass.

[73] Assignee: Thermedics Detection Inc., Chelmsford, Mass.

[21] Appl. No.: 731,573

[22] Filed: Oct. 16, 1996

Related U.S. Application Data

[60] Provisional application No. 60/005,358 Oct. 16, 1995, and provisional application No. 60/005,871 Oct. 26, 1995, and provisional application No. 60/014,185 Mar. 26, 1996, and provisional application No. 60/026,504 Sep. 23, 1996.

[51] Int. Cl.[6] ............................ G01N 30/60; G01N 30/54
[52] U.S. Cl. ......................................... 73/23.39; 73/23.35
[58] Field of Search ............................... 73/23.22, 23.25, 73/23.26, 23.35, 23.36, 23.39, 23.42; 95/82, 87; 96/101, 102, 103, 104; 422/89

[56] References Cited

U.S. PATENT DOCUMENTS

| | | | |
|---|---|---|---|
| 3,053,077 | 9/1962 | Tracht | 73/23.22 |
| 3,062,039 | 11/1962 | Ayers | 73/23 |
| 3,139,745 | 7/1964 | Sievers et al. | 73/23.22 X |
| 3,148,532 | 9/1964 | Broerman | 73/23.25 |
| 3,198,001 | 8/1965 | Ferrin | 73/23.25 |
| 3,366,149 | 1/1968 | Taft et al. | 141/82 |
| 3,537,585 | 11/1970 | Waters | 210/198 |
| 3,581,573 | 6/1971 | Purcell et al. | 73/23.42 X |
| 3,592,046 | 7/1971 | Cramers et al. | 73/23.25 |
| 3,668,834 | 6/1972 | Deans | 55/67 |
| 4,181,613 | 1/1980 | Welsh et al. | 73/23.25 X |
| 4,204,423 | 5/1980 | Jordan | 73/23.25 |
| 4,269,608 | 5/1981 | Sisti et al. | 55/67 |
| 4,650,964 | 3/1987 | Vincent | 219/301 |
| 4,726,822 | 2/1988 | Cates et al. | 55/267 |
| 4,728,776 | 3/1988 | Vincent | 219/301 |
| 4,771,628 | 9/1988 | Sisti et al. | 73/23.25 |
| 4,805,441 | 2/1989 | Sides et al. | 73/23.1 |
| 4,948,389 | 8/1990 | Klein et al. | 55/20 |
| 5,005,399 | 4/1991 | Holtzclaw et al. | 73/23.39 |
| 5,014,541 | 5/1991 | Sides et al. | 73/23.41 |
| 5,024,952 | 6/1991 | Alsop | 436/177 |
| 5,028,243 | 7/1991 | Rubey | 55/67 |
| 5,047,073 | 9/1991 | Stetter et al. | 55/18 |
| 5,048,322 | 9/1991 | Hiller et al. | 73/23.41 |
| 5,096,471 | 3/1992 | Sacks et al. | 55/67 |
| 5,098,451 | 3/1992 | Rounbehler et al. | 55/67 |
| 5,099,743 | 3/1992 | Rounbehler et al. | 86/50 |
| 5,108,705 | 4/1992 | Rounbehler et al. | 422/89 |
| 5,114,439 | 5/1992 | Yost et al. | 55/20 |
| 5,135,549 | 8/1992 | Phillips et al. | 55/67 |
| 5,141,532 | 8/1992 | Sacks et al. | 55/67 |
| 5,152,176 | 10/1992 | Bryselbout et al. | 73/23.41 |
| 5,215,556 | 6/1993 | Hiller et al. | 55/67 |
| 5,224,972 | 7/1993 | Frye et al. | 55/18 |
| 5,268,302 | 12/1993 | Rounbehler et al. | 436/96 |
| 5,300,758 | 4/1994 | Rounbehler et al. | 219/497 |
| 5,310,681 | 5/1994 | Rounbehler et al. | 436/106 |
| 5,437,179 | 8/1995 | Wiegand et al. | 73/23.35 |
| 5,589,630 | 12/1996 | Wiegand et al. | 73/23.35 |
| 5,611,846 | 3/1997 | Overton et al. | 96/102 |

*Primary Examiner*—Michael Brock
*Attorney, Agent, or Firm*—Fish & Richardson P.C.

[57] ABSTRACT

A high speed gas chromatography system includes a heated isothermal region and a gas chromatography column located externally to the isothermal region. The system also includes a detector and a flow path between the column and the detector. At least a portion of the flow path is positioned in the isothermal region.

112 Claims, 19 Drawing Sheets

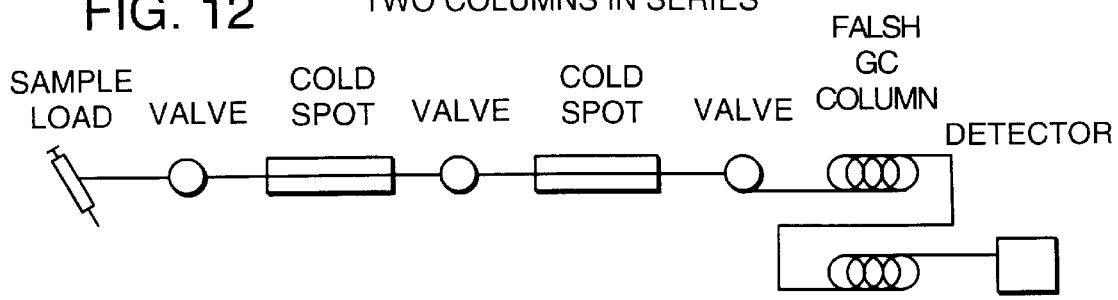
FIG. 12 TWO COLUMNS IN SERIES
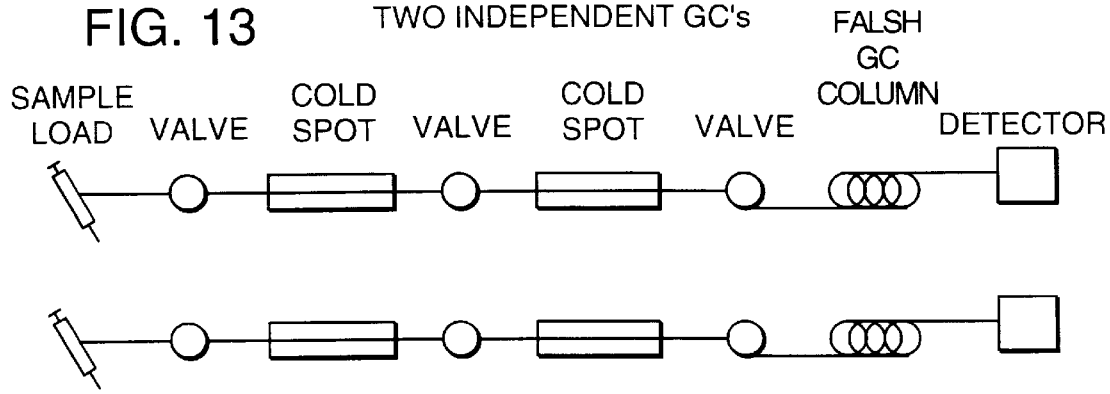
FIG. 13 TWO INDEPENDENT GC's
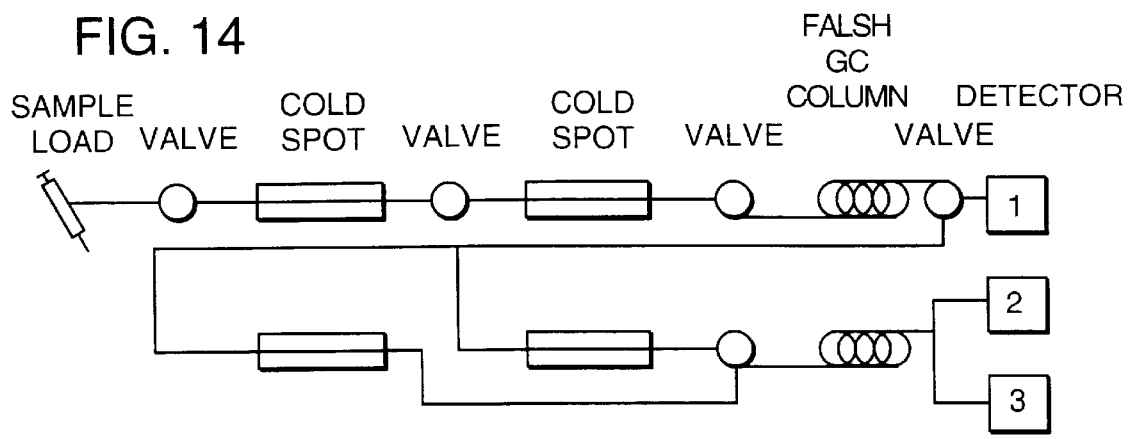
FIG. 14

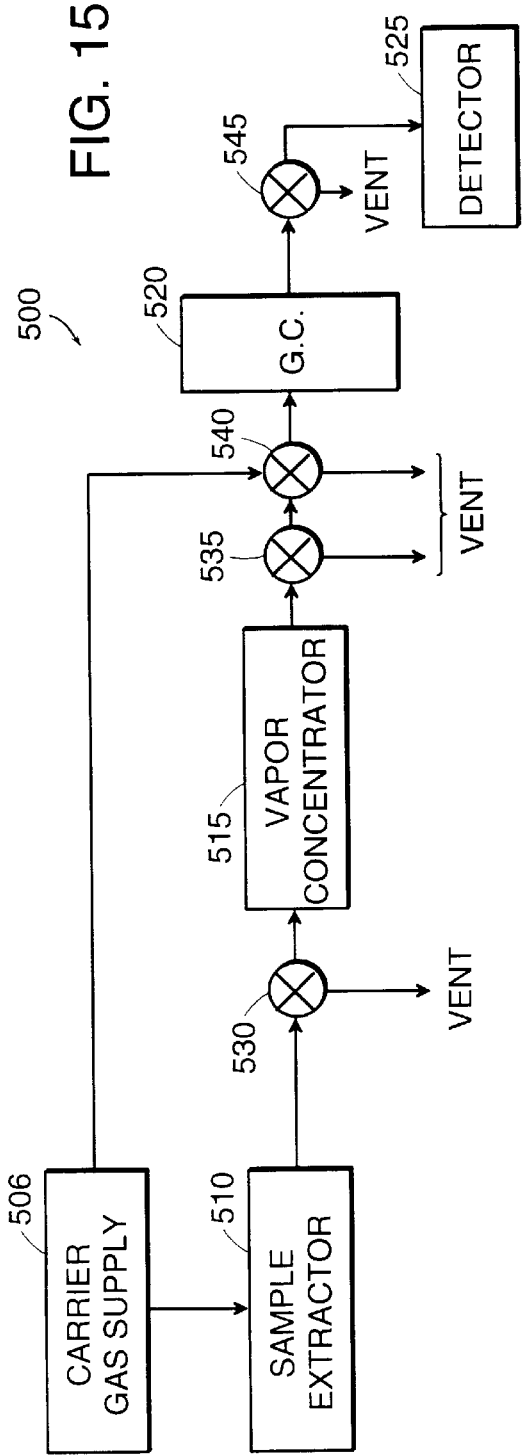
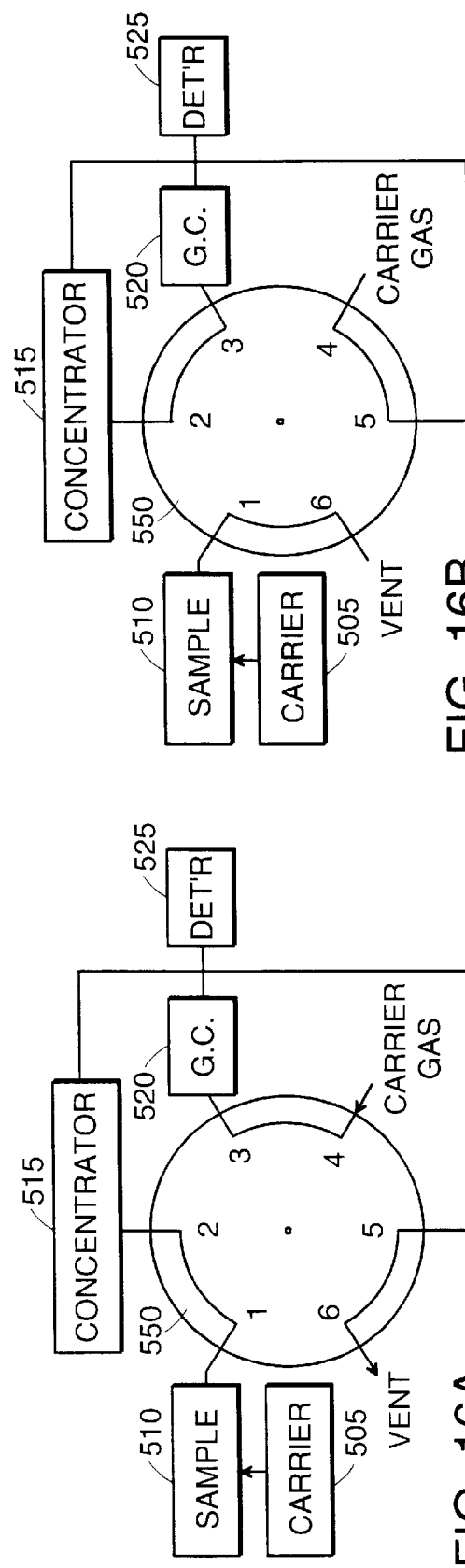

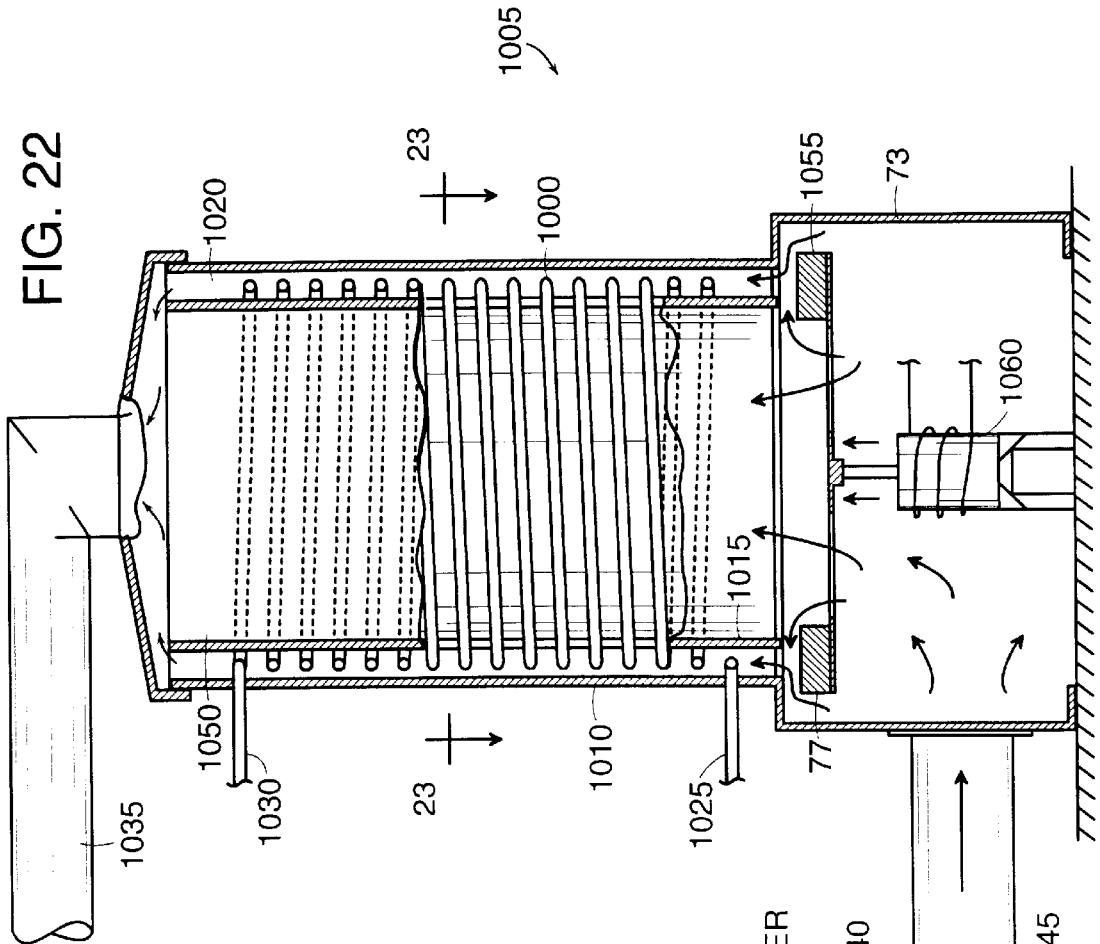
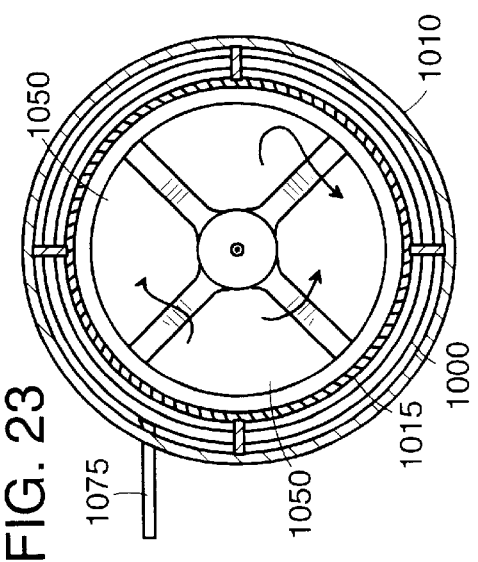
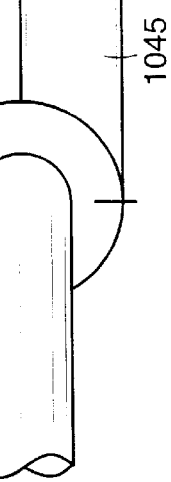
FIG. 22
FIG. 23

HIGH SPEED GAS CHROMATOGRAPHY

CROSS REFERENCE TO RELATED APPLICATIONS

The present invention is related to the subject matter of U.S. Provisional Application No. 60/005,358, entitled "Very High Speed Gas Chromatography" and filed Oct. 16, 1995; U.S. Provisional Application No. 60/005,871, entitled "Flash 2D GC Analyzer System" and filed Oct. 26, 1995; U.S. Provisional Application No. 60/014,185, entitled "Very High Speed Gas Chromatography" and filed Mar. 26, 1996; and U.S. Provisional Application No. 60/026,504, entitled "High Speed Gas Chromatography" and filed Sep. 23, 1996. These applications are incorporated herein by reference.

BACKGROUND OF THE INVENTION

The invention is directed to high speed gas chromatography for detection of various compounds.

Gas chromatography is described in U.S. Pat. Nos. 5,092,155; 5,092,157; 5,098,451; 5,099,743; 5,108,705; 5,268,302; 5,300,758; and 5,310,682. These patents are incorporated herein by reference.

SUMMARY OF THE INVENTION

The invention provides a high speed flash gas chromatography system that provides in one to two minutes results that may require one to two hours of processing by conventional gas chromatography systems. The system includes a heated isothermal region and a gas chromatography column located externally to the isothermal region. The system also includes a detector and a flow path between the detector and the gas chromatography column. At least a portion of the flow path is positioned in the isothermal region.

Embodiments of the invention may include one or more of the following features. The system may include a housing external to the isothermal region, with the gas chromatography column positioned in the housing. The housing may be configured to isolate the gas chromatography column from heat sources external to the housing. To this end, the housing may include an insulating wall between the housing and the isothermal region.

The gas chromatography column may include a conductive metal sheath, and the system may include circuitry for supplying an electrical current to the conductive metal sheath for heating the column. To reduce the amount of heat lost from the sheath to the housing, the interior of the housing is designed to have a low thermal mass. For example, the interior of the housing may include a thin layer of metal floating on a thick layer of thermal insulation. This arrangement also reduces the amount of heat retained by the interior of the housing during successive heating/cooling cycles.

In addition to the conductive metal sheath, the gas chromatography column may include a layer of electrically insulating material surrounding the conductive metal sheath. The material may also provide thermal insulation. For example, the metal sheath may be surrounded by a layer of glass fibers. The gas chromatography column may be coiled for compactness.

The housing also may include a fan for circulating air in the housing to provide homogenous heat distribution within the housing. This air circulation eliminates or reduces the occurrence of a so-called chimney effect that may result when air heated by lower coils of the column rises and heats upper coils of the column.

The housing also may include an inlet configured to operate in an open position that permits flow into the housing through the inlet or a closed position that prevents flow into the housing through the inlet. A control mechanism, such as louvers, may be attached to the inlet and operable to switch the inlet between the open and closed positions. A processor configured to control the system may be connected to the control mechanism and configured to cause the control mechanism to place the inlet in the open position to cool the gas chromatography column.

The system also may include a holder configured to maintain the column in the coiled configuration. For example, the holder may include four side rails and a pair of rings, with the side rails being connected to the rings. Each side rail may includes grooves on a surface of the side rail that is internal to the holder, with each groove being sized to receive a coil of the column.

Heat sinks may be attached to each end of the gas chromatography column. When the isothermal region is an isothermal chamber, the system also may include a fitting positioned in an exterior wall of the isothermal chamber. A heat sink attached to one end of the gas chromatography column may be inserted into the fitting. The system also may include a second fitting positioned in the exterior wall of the isothermal chamber, and a heat sink attached to the other end of the gas chromatography column may be inserted into the second fitting.

The heat sinks may be electrically conductive and attached to the ends of the metal sheath. The fittings may be configured to provide electrical current for heating the column through the attachment of the fittings to the heat sinks.

Other features and advantages of the invention will be apparent from the following detailed description, including the drawings, and from the claims.

BRIEF DESCRIPTION OF THE DRAWINGS

FIGS. 12–14 are schematic views of component configurations in FLASH GC systems.

FIG. 15 is a general block diagram of a high speed gas chromatography system.

FIGS. 16A and 16B are block diagrams illustrating the interconnections achieved by a six-port, two-position valve.

FIG. 22 is a cross-sectional view of a gas chromatography column with a damper control and an apparatus for cooling the column.

FIG. 23 is a cross-sectional view taken along section 23—23 of FIG. 22.

DESCRIPTION OF THE PREFERRED EMBODIMENTS

Figure 1:
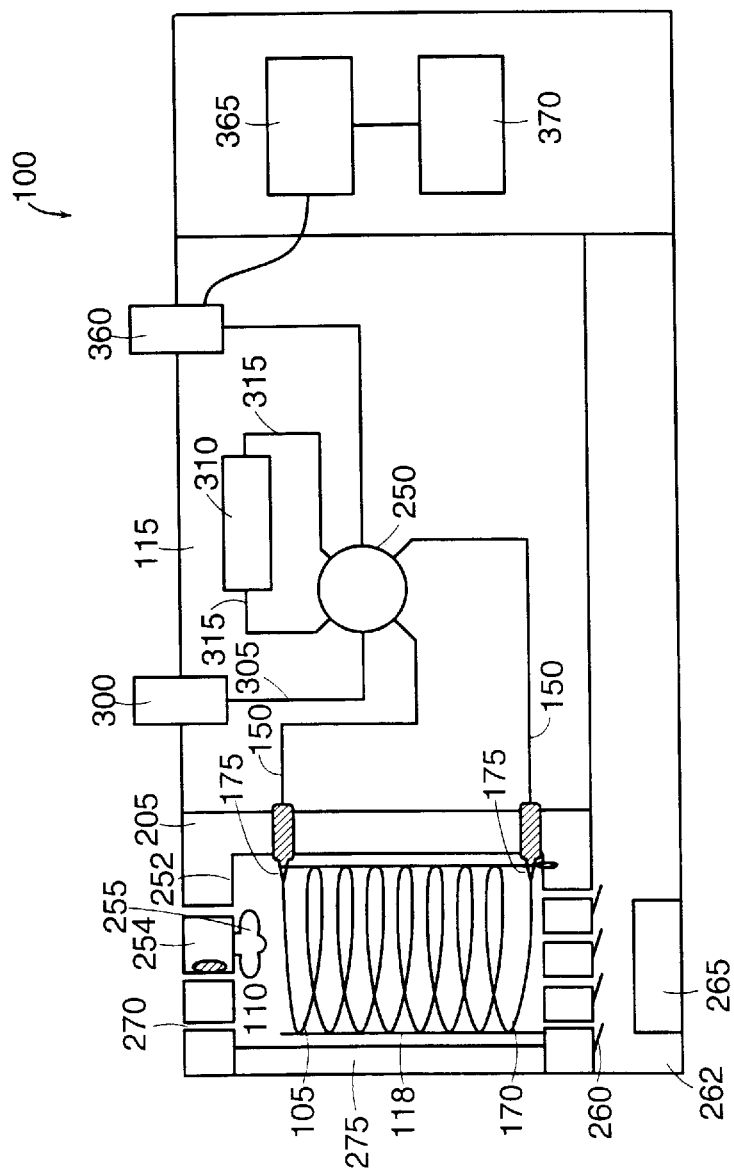
FIG. 1 is a block diagram of a high speed flash gas chromatography system.

With reference to FIG. 1, a high-speed flash gas chromatography system 100 includes a coiled gas chromatography tube 105 located in a column housing 110. Other components of the system 100 are located in a valve oven 115.

Figure 2:
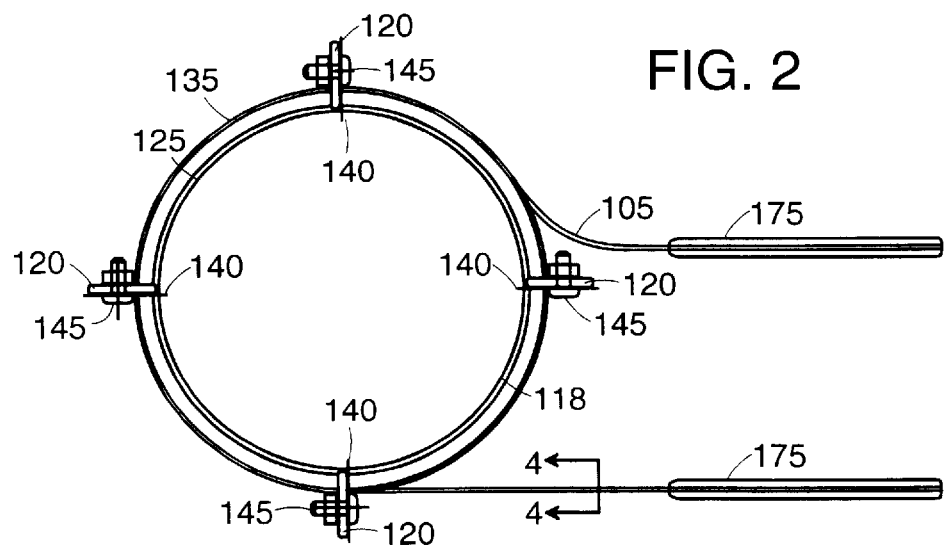
FIGS. 2 and 3 are top and side views of a gas chromatography column of the system of FIG. 1.
Figure 3:
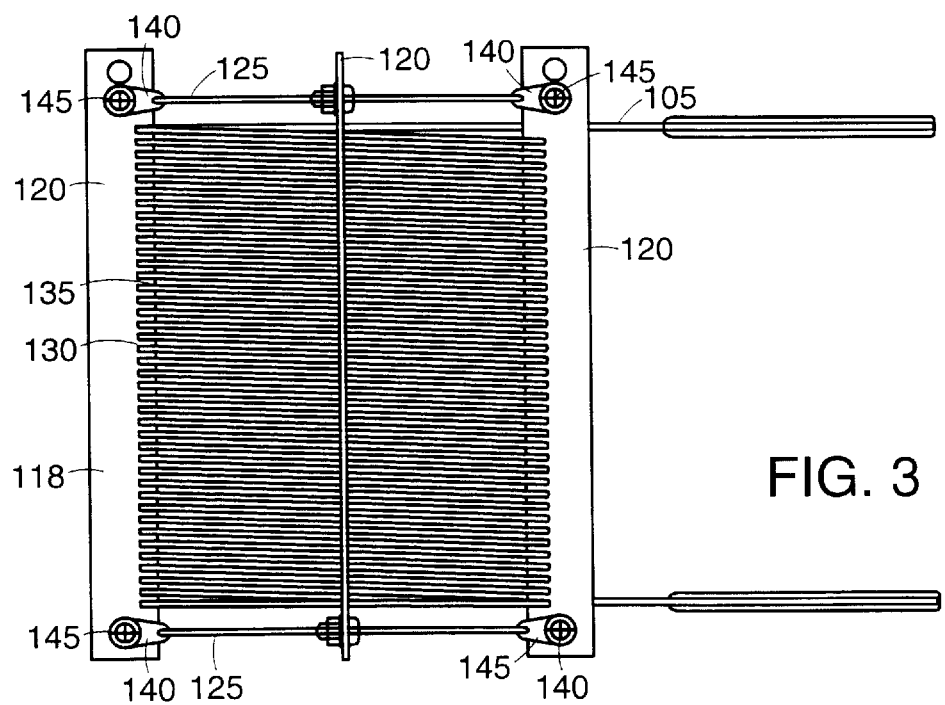

With reference also to FIGS. 2 and 3, the tube 105 is maintained in the coiled configuration by a lightweight holder 118 that is positioned in the column housing 110. To minimize heat loss from the tube 105, the holder 118 is designed to have only minimal contact with the tube 105. To this end, the holder 118 includes four side rails 120 that are connected to a pair of rings 125. The side rails 120 are positioned around the tube 105 and include grooves 130 that are each sized to receive a coil 135 of the tube. Spacing between the grooves 130 controls the vertical spacing between the coils 135. The side rails are made from mica or other electrically and thermally insulative material.

The rings 125, which are made from metal, are smaller in diameter than the coils 135 and are positioned at the top and bottom of the holder 118. Fittings 140 on the rings are attached to the side rails by screws 145. The shape of the rings 125 and the orientation of the side rails 120 relative thereto serves to maintain the coiled configuration of the tube 105.

Figure 4:
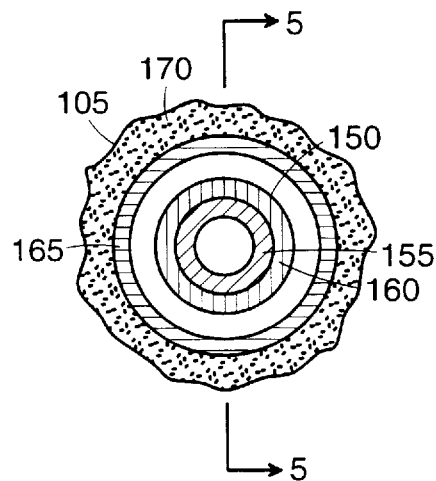
FIG. 4 is a sectional view taken along section 4—4 of FIG. 2.
Figure 5:
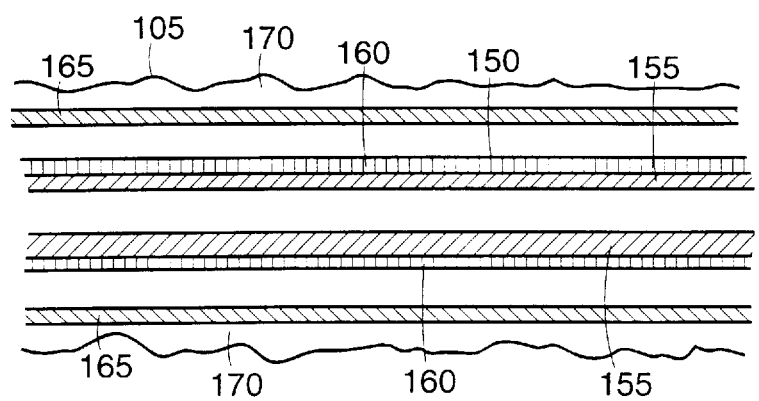
FIG. 5 is a sectional view taken along section 5—5 of FIG. 4.

With reference to FIGS. 4 and 5, the tube 105 includes a gas chromatography column 150 that has a layer of polymer 155 coating an interior surface of a glass or quartz fused silica tube 160. The column 150 is located within a stainless steel sheath 165. The sheath 165 may be rapidly heated by application of an electric current, and is located within an electrically-insulative woven glass sleeve 170. The glass sleeve 170 permits the grooves 130 (FIG. 2) to be spaced so close together that the coils 135 (FIG. 2) can touch one another without producing an electrical short circuit. If the grooves 130 were spaced far enough apart that the coils could not touch, then the glass sleeve 170 would be unnecessary.

To permit insertion of the column 150 into the sheath 165, the outer diameter of the column 150 is smaller than the inner diameter of the sheath 165. The difference between the two diameters must be large enough to permit insertion of the column 150 into the sheath 165, but must be small enough to permit rapid heat transfer from the sheath 165 to the column 150. For example, in one implementation, the column 150 has an outer diameter of 0.5 millimeters while the sheath 165 has an inner diameter of 0.55 millimeters.

Referring again to FIGS. 2 and 3, heat sinks 175 are braised to each end of the sheath 165. The heat sinks 175 prevent the temperature of the ends of the sheath 165 from overshooting a desired temperature when an electric current is applied to the sheath 165 to heat the sheath 165 and the column 150. In extreme cases, this prevents destruction of the portions of the column 150 at the ends of the sheath 165. The heat sinks 175 may be made from brass or other suitably conductive materials.

Figure 6:
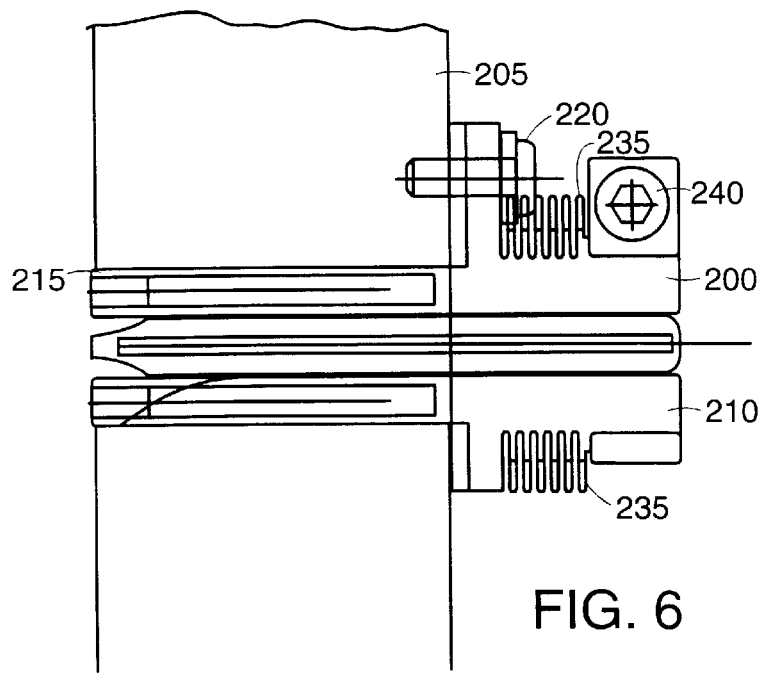
FIGS. 6–8 are views of a fixture of the system of FIG. 1.
Figure 7:
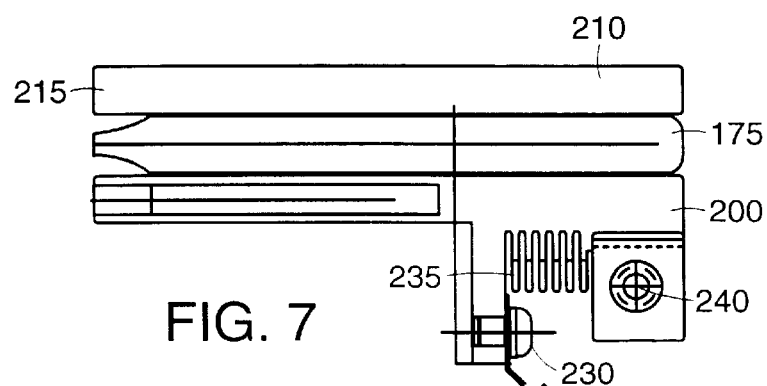
Figure 8:
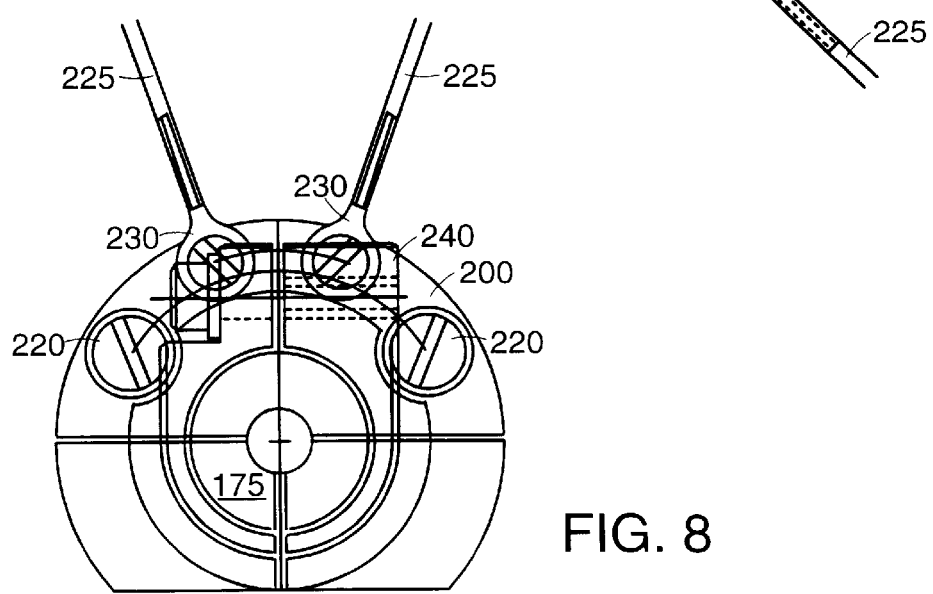

With reference to FIGS. 6–8, each heat sink 175 is configured to be inserted into a fitting 200. The heat sinks 175 provide structural rigidity that assists in placement of the heat sinks within the fittings 200. This simplifies the process of replacing the tube when a column 150 having a different polymer 155 is desired or when a column 150 wears out or is damaged.

As shown in FIGS. 1 and 6, each fitting 200 is attached to a wall 205 between the housing 110 and the valve oven 115. The fitting includes a first section 210 that is positioned within the valve oven 115 and a second section 215 that extends through the wall 205. The first section 210 is secured to the wall 205 by a pair of threaded bolts 220.

Electrical leads 225 are secured to the first section 210 by a second pair of threaded bolts 230. A first electrical lead of each fitting 200 is used to establish a circuit by which an electrical current is applied to the sheath 165 (FIG. 5) to heat the sheath and the column 150. A second electrical lead of each fitting is used to establish a circuit that measures the electrical resistance of the sheath 165. Since the resistance of the sheath 165 varies with temperature, the measurement of the resistance may be used to measure the temperature of the sheath and the column.

Alternative techniques for measuring the temperature of the tube include threading a wire through the sheath 165 and along the column 150, and measuring the resistance of the wire as a measure of temperature. This approach permits the sheath 165 to be made from a material having a resistance that varies little with temperature. Use of such a material provides greater control of the temperature profile through which the sheath 165 can be heated. For example, a linear temperature increase may be obtained much more easily when the resistance varies little with temperature than when the resistance varies greatly with temperature. A temperature sensor also may be produced by coating the column 150 with a layer of metal and, thereafter, measuring the resistance of the metal layer. A metal coating on the column 150 also may be used to replace the metal sheath 165. Similarly, the sheath 165 could be eliminated by using a column 150 having a tube 160 made from metal instead of fused silica. In other alternative approaches, a thermocouple may be placed within the sheath 165 or within the housing 110.

Fins 235 on the exterior of the first section 210 provide heat transfer between the fixture 200 and the interior of the valve oven 115 to maintain the fixture 200 at the temperature of the valve oven 115. As an additional mechanism for maintaining the fixture at the temperature of the valve oven, a heater (not shown) could be included within the fixture. A compression fitting 240 is used to secure the heat sink 175 and the sheath 165 to the fitting 200. As shown in FIG. 1, the ends of the column 150 extend through the heat sinks 175 and the fittings 200 into the valve oven 115. The ends of the column are connected to a valve 250.

Referring again to FIG. 1, use of a separate column housing 110 permits high speed temperature programming of the tube 105 independently of the temperature of the valve oven 115. As noted above, the tube is electrically heated by applying an electric current to the sheath 165 through the heat sinks 175 and their connections to the fittings 200. It has been found that a power supply (not shown) capable of delivering up to 96 Volts at 12 Amps provides sufficient power to heat the tube 105 to desired temperatures.

Heat loss from the tube to air in the housing 110 is reduced by the presence of the glass sleeve 170 overlying the sheath 165 and by dimensioning the housing 110 to conform closely to the dimensions of the coiled tube 105. Heat loss from air to the housing is reduced by reducing the mass of the housing 110. To this end, the interior of the housing includes a thin layer of metal 252 overlying a thick layer of insulation 254. The mass within the housing also is reduced by reducing the mass of the holder 118.

The column housing 110 also provides homogenous heat distribution during heating of the tube 105. Due to constraints on the dimensions of the system 100, the tube 105 is oriented vertically with successive coils stacked atop each other. To prevent the occurrence of a chimney effect (i.e., excessive heating of the upper coils due to rising heat), and to ensure homogenous heat distribution, a small fan 255 circulates air within the column housing 110. The impact of the chimney effect is also reduced by having samples enter the tube 105 at the bottom coil and exit the tube 105 at the top coil. The chimney effect also may be avoided by orienting the tube 105 horizontally with successive coils placed along side each other.

To cool the tube 105, louvers 260 in the bottom of the housing 110 are opened to expose the interior of the housing to a region 262 of positive pressure created by a blower 265 that is positioned beneath the housing 110. When the louvers are opened, air from the region 262 enters the housing 110 and passes out of the housing through slots 270 in the top of the housing 110. The slots 270 are small enough that significant heat is not lost due to air flow through the slots 270 when the louvers 260 are closed. Venting could be accomplished using the fan 255 instead of the blower 265. However, the resulting increase in the mass of the fan would conflict with the goal of reducing the mass within the housing 110.

The housing 110 also includes a door 275. The door may be opened to provide access to the interior of the housing 110 and to the tube 105.

In general, the temperature of the tube 105 is lower than the temperature of the valve oven 115, which is controllable between 50° C. and 400° C. The temperature of the valve oven 115 may be maintained at 300° C. to ensure that samples introduced into the system will be in a vaporized state when not in the tube 105. Whether the samples will be vaporized when in the tube 105 is dependent on the temperature to which the tube 105 is heated.

The system 100 includes an injector 300 that permits introduction of a sample into the system. The injector may be a standard gas chromatography split/splitless injector. An interior surface of the injector is heated to a temperature sufficient to vaporize the sample. A tube 305 connects the injector to the valve 250. When the valve 250 is oriented for sample introduction, the vaporized sample from the injector is carried into the valve.

Figure 9:
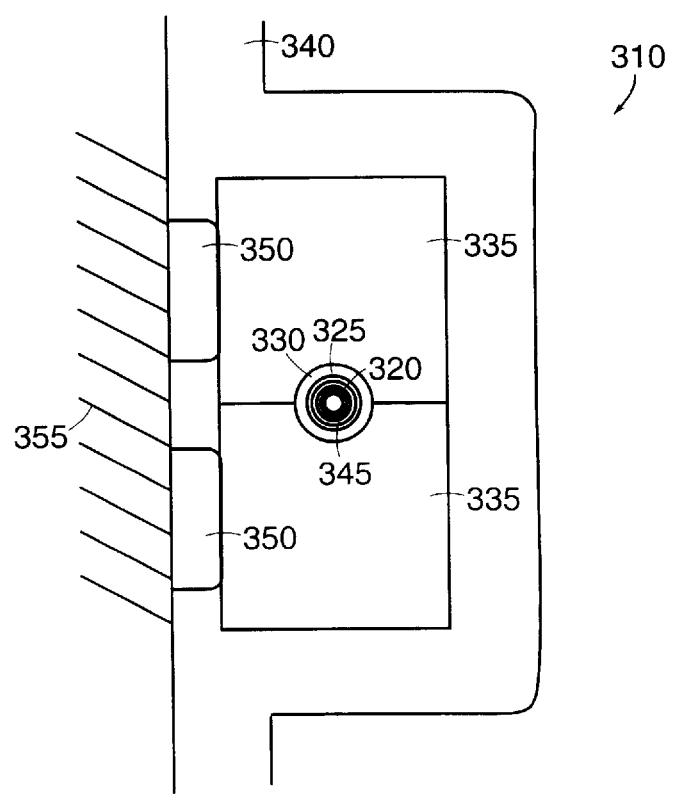
FIG. 9 is an end view showing orientation of a cold spot of the system of FIG. 1.

With reference to FIGS. 1 and 9, a cold spot 310 (also referred to as a vapor concentrator) is connected to the valve 250 by a pair of tubes 315. In essence, the cold spot 310 is a short gas chromatography column 320 that may be cooled rapidly to concentrate vapors and may be heated rapidly to release the concentrated vapors. Like the tube 105, the column 320 is surrounded by a metal sheath 325 that may be heated through application of an electrical current.

The column 320 is positioned within a slot 330 in a block 335 of thermally conductive material (e.g., aluminum) that is itself embedded in a rear wall 340 of the valve oven 115. A layer of silicone 345 is extruded into the slot 330 to surround the sheath and provide electrical insulation as well as some thermal insulation. The block 335 provides a large thermal mass and maintains the column 320 at a constant temperature when no current is applied to the sheath 325.

The block 335 is maintained at a low temperature by a pair of Peltier coolers 350. Heat sinks 355 on the exterior of the rear of the valve oven dissipate heat from the Peltier coolers. The Peltier coolers are able to cool the block 335 to a temperature that is about 25° C. less than room temperature, and is essentially independent of the temperature of the valve oven 115. Thus, when room temperature is 30° C., the temperature of the block may be maintained at 5° C. This is true even when the temperature of the valve oven 115 is 400° C.

Vapors entering the cold spot become entrapped on the polymer coating the interior of the column 320. Less volatile compounds become entrapped immediately upon entering the cold spot, while more volatile compounds travel further along the interior of the column 320 before becoming entrapped.

Compounds are released from the column 320 by applying an electrical current to the sheath 325 to heat the sheath 325 and the column 320. Prior to heating the column 320, the valve 250 may be adjusted to reverse the flow through the column 320. This increases the likelihood that compounds of different volatility will exit the column 320 at or near the same time. In particular, more volatile compounds, which will be released from the polymer sooner, will have a longer distance to travel before exiting the column 320 because they will have travelled further into the column before becoming entrapped. By contrast, less volatile compounds, which will be released from the polymer later, will have a shorter distance to travel before exiting the column 320 because they will have travelled a shorter distance into the column before becoming entrapped.

The system 100 also includes a gas chromatography detector 360. The detector 360 is a standard flame ionization detector, with the exception that electronics 365 associated with the detector operate much faster to provide a higher sampling rate than is provided by electronics that are associated with standard detectors. Typically, about ten data samples are needed to define a peak. Since the system 100 operates at least an order of magnitude faster than traditional gas chromatography systems, the sampling rate may need to be an order of magnitude higher than sampling rates associated with data systems for standard gas chromatography systems. Other suitable detectors include photo-ionization detectors, electron capture detectors, mass spectrometers, pulse ionization detectors and mass selective detectors.

The valve oven 115 is similar to a traditional gas chromatography oven. However, unlike traditional gas chromatography ovens, which need to provide a controlled temperature profile for the gas chromatography column, the valve oven 115 only needs to maintain a single temperature. Accordingly, the valve oven 115 may be simpler and less expensive than traditional gas chromatography ovens.

The system 100 is controlled by a processor 370. The processor 370 controls the temperature of the gas chromatography tube 105 and the temperature of the cold spot 310. In particular, the processor 370 measures the temperature of the tube 105 and controls the electric current supplied to the sheath 165 through the heat sinks 175 to heat the tube 105. The processor 370 also controls the louvers 260 to cool the tube 105 when appropriate. The processor 370 controls the cold spot 310 in a similar manner.

The processor 370 also controls flow through the system 100 by controlling the valve 250. For ease of illustration, the valve 250 is pictured and discussed as a single valve. In reality, the valve may include multiple valves and may include additional connections to, for example, a supply of carrier gas (not shown) and a vent (not shown). The important issue is that the valve (or valves) must be controllable by the processor to control flow through the system in a desired manner. For example, the processor may initially configure the valve so that samples from the injector 300 flow through the cold spot 310 before being vented to atmosphere. When a sufficient quantity of the sample is collected by the cold spot 310, the processor reconfigures the valve so that flow through the cold spot 310 is reversed and samples exiting the cold spot enter the gas chromatography tube 105.

For ease of description, the system 100 was described above as including a single gas chromatography tube 105 and a single cold spot 310. However, actual implementations of the system may include additional gas chromatography tubes and cold spots, as well as multiple injectors and multiple detectors. For example, the FLASH Gas Chromatography System ("the FLASH GC") available from Thermedics Detection, Inc. of Chelmsford, Mass. (the assignee of this invention) includes two gas chromatography columns and up to four cold spots. The gas chromatography columns can be temperature programmed to heat and cool independently of each other, and provide heating rates from 1° C. per second to 100° C. per second. The cold spots can be temperature programmed to heat and cool independently of each other, and provide heating rates as fast as 6000° C. per second. The FLASH GC provides resolution of peak widths of less than 100 milliseconds, and may run complex chromatograms in less then one hundred seconds.

Conventional gas chromatography conditions serve as a guide to selecting the best columns and operating parameters. Once the machine is plumbed for the application, a processor manipulates the FLASH GC. Temperature profiles and valve timing sequences are controlled using a keyboard. Gas chromatography operating conditions can be evaluated and tested quickly.

In the FLASH GC, the sample introduction step is isolated from the gas chromatography columns, which allows both processes to be optimized for maximum performance. A samples is introduced onto a cold spot that concentrates and focuses the sample prior to introduction of the sample into the gas chromatography column. As noted above, the cold spot is a short length of either fused silica or metal tubing, much like regular gas chromatography tubing. The tubing, which is about 10 cm long, has a special metal sheath, so that it can be rapidly and reproducibly cooled and heated under processor control.

The temperature of the cold spot is held constant across its length. The rate of temperature rise (or fall) across its entire length is controlled by the operator using the processor. Virtually any heating profile (including increasing, flat and decreasing temperature) can be selected. The processor updates and monitors the temperature profile every millisecond. Heating rates are very fast, from 4° C. per second to 6000° C. per second.

Figure 10A:
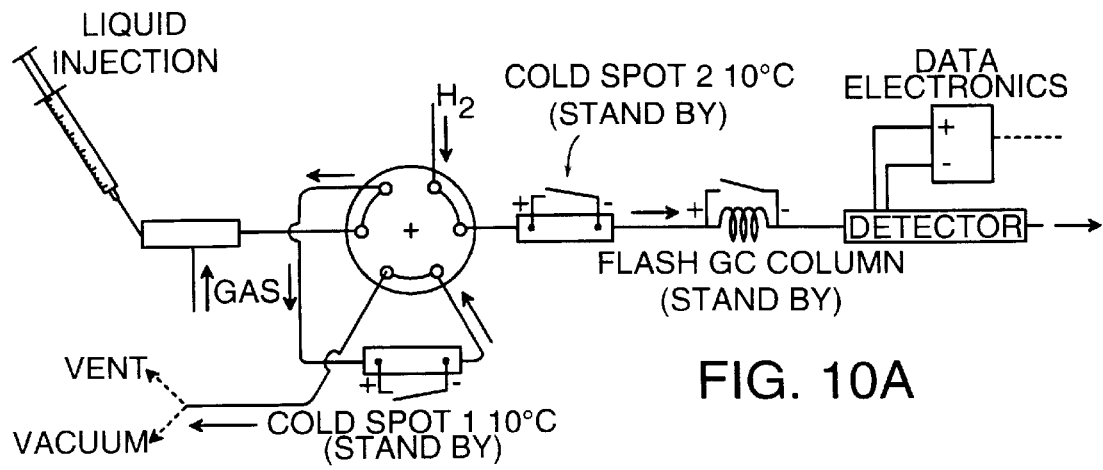
FIGS. 10A–10C are schematic views of component configurations in a FLASH GC system.
Figure 10B:
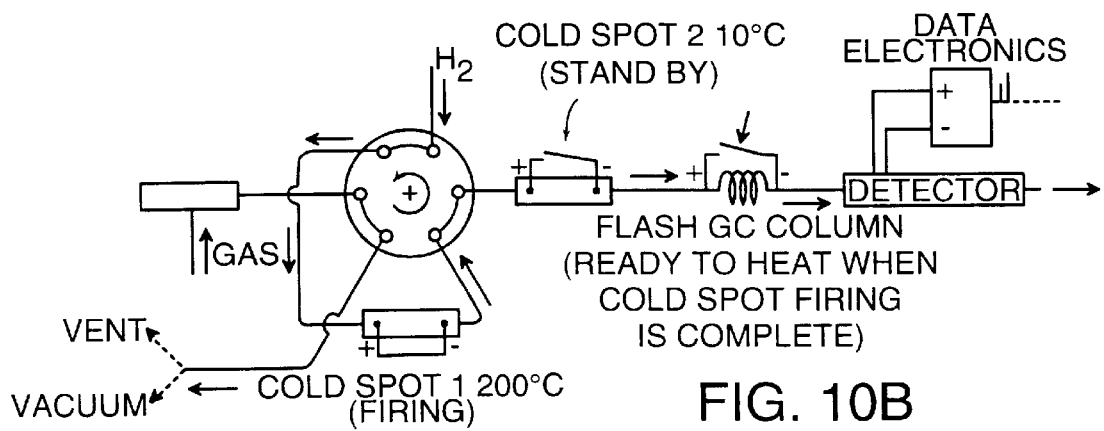
Figure 10C:
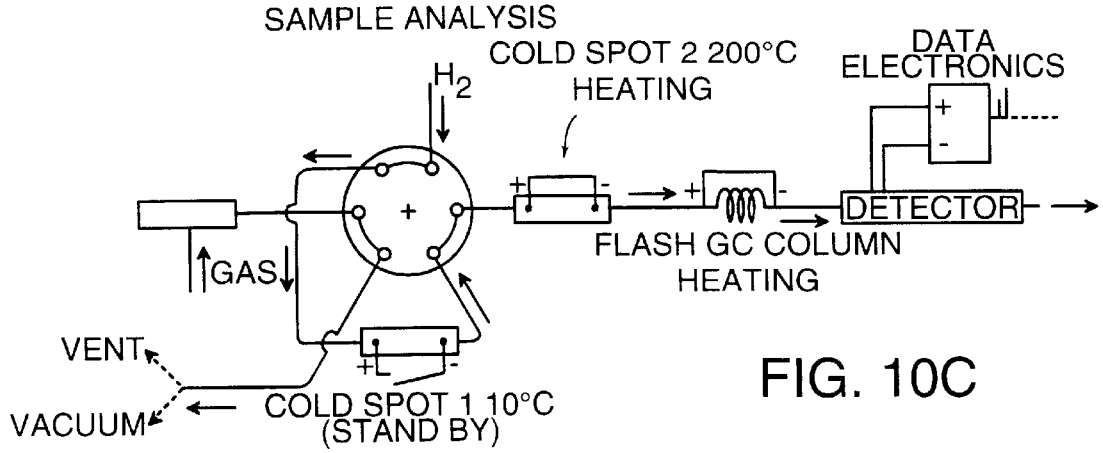

Isolation of the sample introduction process from the gas chromatography column allows for simultaneous and independent optimization of the sample inlet stage and the gas chromatography columns, without cross talk between the two stages. FIGS. 10A–10C show dual cold spots arranged in series and isolated from the gas chromatography column. The first cold spot is used to collect the sample, and the second cold spot is used to tightly focus sample prior to analysis. FIG. 10A shows the system in a configuration suitable for collecting a sample. As shown, carrier gas and the sample from the injector pass through the valve and the first cold spot before being vented to atmosphere. At the same time, a carrier gas passes through the valve, the second cold spot, the column and the detector to purge those components of the system. As shown in FIG. 10B, in a sample focusing configuration, the first cold spot is heated and the valve is adjusted so that the desorbed sample from the first cold spot is collected by the second cold spot. Finally, as shown in FIG. 10C, in a sample analysis configuration, the second cold spot is heated so that the desorbed sample from the second cold spot enters the column. The arrangement illustrated in FIGS. 10A–10C may be used, for example, to concentrate and pool samples from multiple injections at the second cold spot, and to then analyze the combined samples, to thereby boost the amount of sample that is introduced onto the gas chromatography column.

Figure 11A:
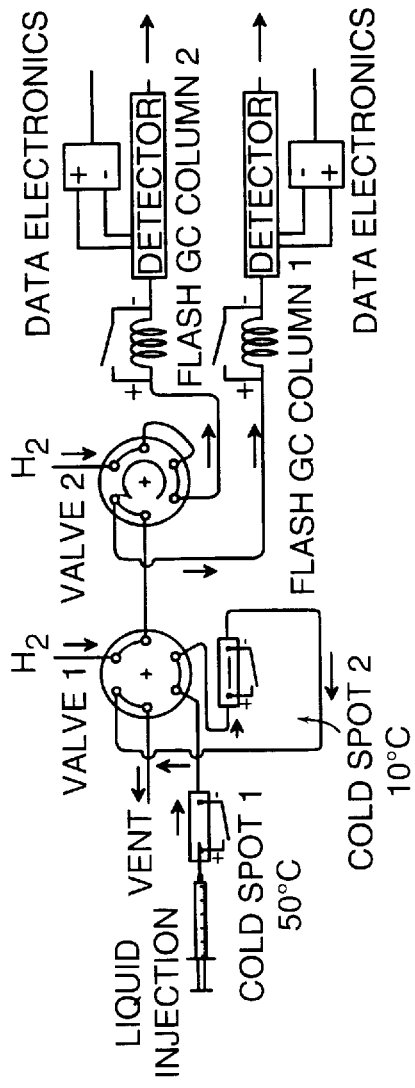
FIGS. 11A–11D are schematic views of component configurations in a FLASH GC system.
Figure 11B:
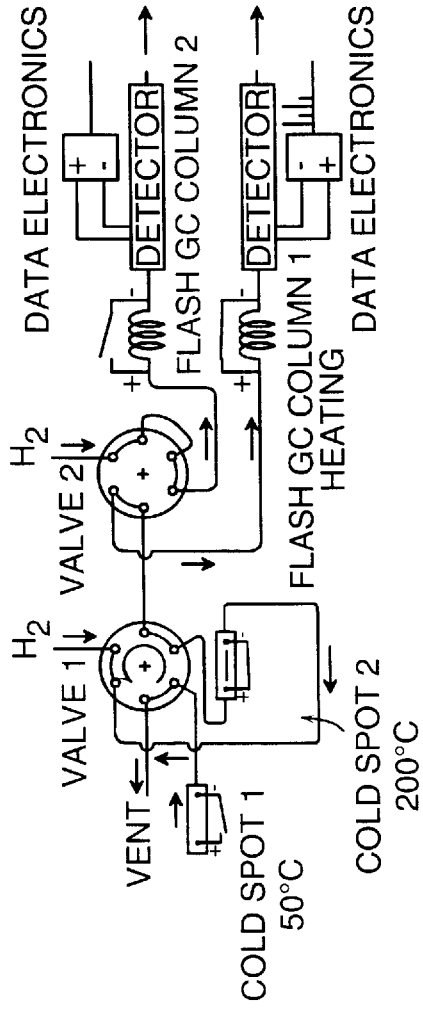
Figure 11C:
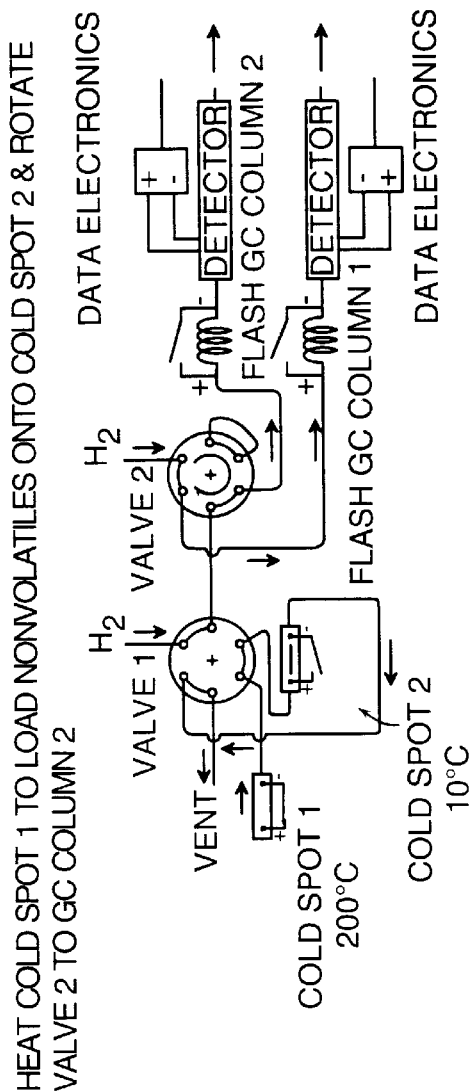
Figure 11D:
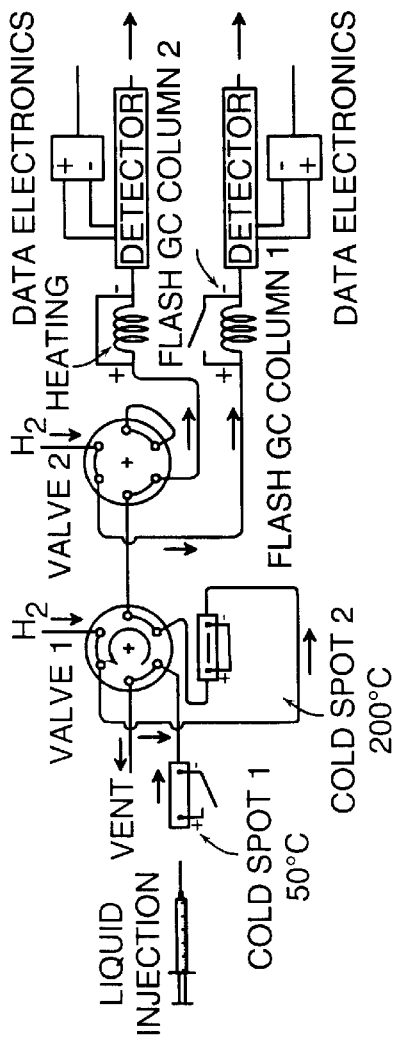

The cold spots focus the sample as a small band for very fast and reproducible introduction to the gas chromatography column. For the smallest peak widths, the cold spot is desorbed in the reverse direction. A flow schematic for this application is shown in FIGS. 11A–11D. As shown, the system includes two cold spots, two valves, and two gas chromatography columns arranged in parallel. In FIG. 11A, the system is configured for sample introduction. Less volatile compounds are trapped by the first cold spot, which is cooled to 50° C., while more volatile compounds are trapped on the second cold spot, which is cooled to 10° C. Carrier gas is directed through the gas chromatography columns and their associated detectors to purge those components. In FIG. 11B, the second cold spot is heated and the first valve is adjusted to permit analysis of desorbed materials from the second cold spot by the first gas chromatography column and its associated detector. In FIG. 11C, first cold spot is heated, the second cold spot is cooled, the first valve is rotated to permit capture by the second cold spot of desorbed materials from the first cold spot, and the second valve is rotated to permit subsequent transfer from the second cold spot to the second gas chromatography column. Finally, in FIG. 11D, the second cold spot is heated and the first valve is adjusted to permit analysis of desorbed materials from the second cold spot by the second gas chromatography column and its associated detector. Typical peak widths, depending upon operation, may be from 100–200 milliseconds. The operator selects the precise time in the process for rapidly introducing the sample onto the gas chromatography column. Because the compound of interest is typically in the hot zone of the gas chromatography column for only a few seconds, thermally labile compounds, which are not normally amenable to gas chromatography, can often be analyzed.

As shown in FIG. 12, the two gas chromatography columns can be arranged and operated in series. Alternatively, as shown in FIG. 13, with two injectors, the FLASH GC can be configured to run two entirely different analyses simultaneously, so as to serve as two separate very fast gas chromatography systems.

Each gas chromatography column is metal sheathed, which allows it to be rapidly and reproducibly heated at heating rates up to 100° C. per second. In addition to rapid heating, rapid cooling of the column can be used as part of the temperature profile. For example, chromatography on the first column can be temporarily frozen by rapidly cooling the column while the second column completes its high speed chromatogram. The first column can then be heated with a square wave profile to regain its previous temperature, and then allowed to continue with its temperature profile. In addition, various fractions from the first column can be collected on one or more cold spots, which can then be analyzed, in turn, by the second column. The block flow diagram for this arrangement is shown in FIG. 14.

An additional advantage of the very fast heating rates is that the gas chromatography column can be baked out at the end of each chromatogram by heating the gas chromatography column up to the maximum temperature of the column materials. The gas chromatography column is thereby cleansed prior to the next analysis. This feature allows for tens of thousands of analyses per gas chromatography column without degradation.

FIG. 15 provides a generalized block diagram of a high speed gas chromatography system 500 similar to the system 100 discussed above. Major components of the system include a carrier gas supply 505, a sample extractor 510 (which corresponds to the injector 300 of the system 100), a vapor concentrator 515 (which corresponds to the cold spot 310 of the system 100), a gas chromatography column 520, and a detector 525.

The carrier gas supply 505 produces heated carrier gas and supplies the carrier gas to the sample extractor 510. Suitable carrier gases include air, hydrogen, helium, and other gases that are inert with respect to the processes used by the system 500.

The sample extractor 510 provides the sample to be analyzed. The sample may be a liquid or gas sample. Alternatively, the sample extractor may contain materials to be analyzed, such as, for example, grains (e.g., wheat kernels) or other granular materials that are contaminated with substances to be detected (e.g., pesticides). As the heated carrier gas passes through the materials to be analyzed, the carrier gas extracts a vapor sample from the materials and carries the vapor sample out of the sample extractor 510.

The sample extractor 510 is shown by way of example. The vapor sample and carrier gas supplied to the system may be prepared by other suitable means. For example, the carrier gas could be passed over a metal support covered with a gas chromatography polymer material on which organic compounds previously had been trapped.

Upon exiting the sample extractor 510, the vapor sample and the carrier gas pass through a valve 530 before entering the vapor concentrator 515. The vapor concentrator 515 may be identical or similar to the cold spot 310 discussed above. In addition, the vapor concentrator 515 may be of the form shown in U.S. Pat. No. 5,098,451, which is incorporated herein by reference. In some systems, the vapor concentrator 515 could be removed or replaced with several vapor concentrators arranged sequentially or in parallel.

In general, the vapor concentrator 515 may be formed from a short gas chromatography column configured to be rapidly heated or cooled. For example, the vapor concentrator may be formed from glass tubing lined with gas chromatographic material suitable to adsorb the substances of interest from the carrier gas stream and positioned in a length of small-diameter metal tubing (e.g., stainless steel needle-stock tubing).

As the carrier gas and the vapor sample pass through the concentrator 515, the vapor sample is adsorbed by, and concentrated in, the chromatographic material lining the concentrator. The carrier gas and any remaining vapor sample are vented to atmosphere by a valve 535 upon exiting the concentrator 515.

While the vapor sample is being concentrated in the concentrator, carrier gas from the carrier gas supply 505 is supplied to the gas chromatography column 520 through a valve 540. The carrier gas purges the column 520 and restores the column to ambient temperature. Upon exiting the column 520, the carrier gas is vented to the atmosphere through a valve 545.

The gas chromatography column 520 may be identical or similar to the tube 105 of the system 100. Another suitable gas chromatography column is described in U.S. Pat. No. 5,098,451, which is incorporated herein by reference. In general, the gas chromatography column 520 may be formed similarly to the concentrator 515 described above, but may be of a longer length (e.g., 1 to 18 meters long). For compactness, the column may be coiled as a compact helix. Coiling of the column also helps to prevent breakage of the column due to heat expansion.

When a sufficient amount of the vapor sample has been adsorbed by the concentrator 515, the concentrator is rapidly heated by applying an electric current to the metal tubing. In particular, the concentrator is rapidly heated to a temperature sufficient to desorb the substances that previously were adsorbed by the concentrator so that those substances are then ejected into the carrier gas stream as a concentrated sample. The ejected sample may form a short burst or plug lasting for 25 to 100 milliseconds. The temperature to which the concentrator 515 is heated is insufficient to decompose materials of interest in the sample.

As the concentrator 515 is heated, the valves 535 and 540 are reset so that the carrier gas and desorbed materials from the concentrator pass through the valves and enter the gas chromatography column 520. In the gas chromatography column 520, constituents of the desorbed materials are time-separated so that different constituents leave the gas chromatography column at different times.

After passing through the gas chromatography column, the carrier gas stream containing the spaced constituents passes through the valve 545 and enters the detector 525. Like the detector 360, the detector 525 may be a flame ionization detector, a thermal conductivity detector, or another detector commonly used in gas chromatography. The detector 525 provides an indication of vapor concentrations at different times. Since the time required for different materials to travel through the gas chromatography column is known, the relative concentration of a particular material in the sample may be determined by examining the signal produced by the detector at the time corresponding to that material.

In some instances, the detector 525 may include a pyrolyzer that breaks down certain constituents of the sample vapors into compounds that are more readily detected by the detector, while leaving other constituents unaffected. For example, when the system is configured to detect nitrogen compounds, the detector may include a pyrolyzer configured to break down the nitrogen compounds into nitrous oxide.

The valves 530, 535 and 540 may be ganged to operate simultaneously or may be formed from a single high-speed, 6-port, two-way valve 550, as shown in FIGS. 16A and 16B. The valve 550 is a rotary switching valve that has two positions (A and B) between which the valve can be exchanged in as little as 50 to 150 milliseconds.

The valve 550 has six ports designated by numerals 1 to 6. The output of the sample extractor 510 is connected to port 1. The vapor concentrator 515 is connected between ports 2 and 5. The gas chromatography column 520 is connected to port 3. The carrier gas supply 505 is connected to port 4, and the connection to port 6 is vented to atmosphere.

In position A, as shown in FIG. 16A, the valve 550 connects together ports 1 and 2, ports 3 and 4, and ports 5 and 6. With this arrangement, the output of the sample extractor 510 is connected (through ports 1 and 2) to one end of the concentrator 515 and the other end of the concentrator 515 is vented to atmosphere (through ports 5 and 6). Thus, vapor samples are concentrated in the concentrator 515 when the valve is in position A. At the same time, the gas chromatography column 520 is connected (through ports 3 and 4) to the source of carrier gas 505, so that carrier gas purges the column 520.

After a sufficient sample has been collected by the concentrator 515, which may occur in as little as 1 to 10 seconds, the valve 550 is switched to the position B shown in FIG. 16B. In this position, the valve 550 connects together ports 1 and 6, ports 2 and 3, and ports 4 and 5. Accordingly, the carrier gas and vapor samples from the sample extractor 510 are vented to atmosphere through ports 1 and 6. Also, carrier gas from the carrier gas supply 505 enters the vapor concentrator 515 (through ports 4 and 5) and, upon exiting the concentrator, enters the gas chromatography column 520 (through ports 2 and 3) and the detector 525. When the valve 550 is in position B, the direction of flow through the concentrator 515 is reversed relative to the direction of flow when the valve is in position A. If desired, a second concentrator may be interposed between port 3 and the gas chromatography column 520.

Once the valve 550 is switched from position A to position B, the concentrator 515 is heated rapidly under computer control. As a result, vapor samples that had previously been adsorbed by the lining of the concentrator 515 are desorbed and transferred to the gas chromatography column 520 in a tight plug with good spatial coherence.

Vapors exiting the gas chromatography column 520 are supplied to the detector 525. The output of the detector 525 may be supplied to a host computer (not shown) for graphical display of the constituents of the sample analyzed by the detector.

The valves 530, 535, 540 and 545 (or the 6-port valve 550), together with the vapor concentrator 515 and the detector 525 may be housed in a heated, insulated enclosure or oven. The oven serves to keep the valves, the tubing that connects them, and the detector hot enough that vapors from the sample are transported efficiently and do not adhere to surfaces of the system components. The appropriate temperature of the oven, which is selected to provide efficient transport without causing breakdown of compounds of interest, varies with the material to be analyzed, and is typically in the range of 150°–300° C.

Various improvements in the operation and structure of very high speed gas chromatography systems, such as the systems shown in FIGS. 1 and 15 and related systems having multiple gas chromatography columns and vapor concentrators, are discussed below. Such improvements, particularly to the heating, cooling and construction of the gas chromatography columns and concentrators, provide enhanced control of gas chromatography analyses. As a result, the improvements permit rapid and accurate analysis of the contents of successive vapor samples. In the following discussion, references to heating and cooling gas chromatography columns apply equally to the gas chromatography columns used in sample analysis and the gas chromatography columns included in the vapor concentrators.

The Gas Chromatoaraphy Column

In general, a gas chromatography column that is being rapidly heated should be continuous and should not include any junctions such as tube-to-tube or tube-to-valve junctions. A junction tends to have increased mass that heats non-uniformly during rapid dynamic heating. This non-uniform heating may result in gas leaks at the junction that are difficult to find and may, in turn, lead to inaccurate chromatography. Leaks may be avoided entirely by dynamically heating a single tube without junctions and, as discussed above with respect to FIG. 1, locating all junctions and connections in an isothermal oven.

As noted above, the metal sheath surrounding the gas chromatography column may be used as the gas chromatography column. To achieve this, the inside of the metal tube must be deactivated, passivated or otherwise coated such as is done for J&W ProSteel or Restek SilcoSteel tubing or for a glass-lined tube. Once the interior surface of the metal tube has been properly treated, a gas chromatography stationary phase is applied directly to the interior surface. Electrical connections are made directly to the metal tube so that the tube may be resistively heated. Use of the metal tube as the column provides more direct heat transfer to the stationary phase since intervening layers of air and other materials are removed.

A problem associated with use of a metal tube such as a ProSteel tube or a SilcoSteel tube is that the resistance of the tube is very low, which may result in difficulties in measuring changes in resistance due to temperature changes. To alleviate this problem, the outside of the metal tube may be coated with a thin layer of electrical insulation (e.g., polyamide) on which is coated a thin layer of metal (e.g., nickel). The thin outer layer of metal would exhibit a relatively large change in resistance with temperature, and the resistance of the thin outer layer could be monitored as a measure of the temperature of the inner, resistively heated metal tube. Use of a separate metal layer for measuring the resistance also will simplify the circuit used to control heating of the metal tube.

An alternative approach to using a metal sheath to heat the gas chromatography column is to wrap the gas chromatography column with wire and resistively heat the wire. This may be implemented in several ways. First, the wire may be wrapped directly on the gas chromatography column. Second, the wire may be wrapped around a thin-walled non-conductive sheath in which the column is positioned, which would allow rapid replacement of the gas chromatography column. Third, the wire may be positioned within a non-conductive sheath that also contains gas chromatography column, which would reduce the thermal barrier between the wire and the gas chromatography column.

In another alternative approach, the column is directly coated with conductive metal that then is resistively heated to heat the column. This eliminates the air gap (and the resulting delay in heat transfer) between the heated metal and the column. Gas chromatography columns previously have been directly coated with metal, most notably aluminum, to extend the useful temperature range of the columns. Though attempts have been made to resistively heat aluminum clad capillary columns, these attempts have failed because aluminum tends to oxidize and because the thickness of the aluminum coating was not sufficiently uniform along the length of the column. Both of these conditions result in "hot spots" and non-uniform heating of the column. The uniformity of the metal layer thickness may be increased by applied the metal layer directly to the fused silica of the column. Oxidation may be prevented by coating the aluminum with a layer of polymer.

Heating and Cooling the Gas Chromatography Column

The key to high speed gas chromatography is to very rapidly heat and cool the column. For this purpose, the thermal mass of the column and the thermal mass that must be heated along with the column must be kept as small as possible. In addition to the electrical heating technique discussed above, other techniques for heating the gas chromatography columns also may be used.

Heating Techniques

One technique uses infrared radiation to heat the gas chromatography column. With this technique, the column is coated with a material that absorbs a wavelength of infrared energy that is emitted by an infrared source. Energy from the infrared source is focused on the column so that the column absorbs the energy and is heated by the absorbed energy. An advantage of this technique is that radiant heat transfer is virtually instantaneous (i.e., at the speed of light), and the only time delay associated with this technique would result from heating the glass or quartz tubing of the gas chromatography column once the energy had been absorbed by the coating material.

Another technique uses microwave energy to heat the column. The column is coated with a material that absorbs microwaves energy and, thereafter, is heated rapidly through exposure to microwaves from a microwave source. For example, a thin metal film may be placed on the outside of the glass or quartz tubing of the column. This metal film absorbs the microwave energy to heat the column. Cooling is accomplished by blowing air across the surface of the column.

Radio frequencies, such as are used to heat metal for welding, may be used to heat the column. A coil is placed around the column and high frequency radio energy is applied to the coil. This technique is extremely fast and does not require a large thermal mass. Cooling is accomplished by blowing air across the surface of the column.

An additional heating technique is to fire electrons at the surface of the column so that the impact of the electrons causes rapid heating. This technique would be particularly useful with shorter length columns.

Laser heating may be accomplished by using the quartz tube of the column as a light path along which infrared energy from a laser is transmitted. Coatings within the column are immediately and rapidly heated due to absorption of some of the laser energy.

Combustive heating may be employed using natural gas or propane fuels to achieve rapid heating. The column may be heated by applying a flame directly to the column, or by providing the column with a catalytic surface. For example, the outside of the column may be coated with a catalytic material so that a gas, or other reactive compound, flowing over the catalytic surface is absorbed and decomposed to generate heat that is transferred to the column. The column is cooled by turning off the flow of gas and passing air across the surface of the column.

High pressure steam may be used to transfer heat rapidly to the column. This technique uses concentric tubes in which the outer tube contains high pressure steam and the inner tube contains (or is) the column. This technique would require a separate boiler and pressure system plus the piping necessary to pipe the steam.

Cooling Techniques

In addition to heating the column during an analysis cycle, a system must be able to cool the column to a desired equilibrium temperature prior to initiating the analysis cycle. The period required to achieve this cooling, which may be referred to as the recovery time, should be short to provide large sample throughput. In addition, it is often desirable to have a reproducible starting temperature. If the cooling technique is fast enough, it may be sufficient to cool the column, possibly to below the desired temperature, and then to raise the temperature to the desired starting temperature just before initiating the analysis cycle.

Lack of an effective cooling technique has been an impediment to achieving truly high speed gas chromatography. In particular, high speed gas chromatography systems may need to obtain results repetitively in less than 5 to 30 seconds. Since the temperature of the column must be reduced between successive analyses, the cooling mechanism must be able to cool the column in substantially less than the analysis repetition time. For example, after running a temperature-programmed or high-temperature chromatogram, the gas chromatography column must be returned to its initial low (usually ambient) temperature before the next sample can be analyzed. Previously, this temperature reduction has been achieved by blowing ambient or cooled air or other gas (such as carrier gas) over the gas chromatography column using a fan or blower. However, such fans and blowers typically have inertia that causes them to coast for a few seconds after they are turned off. This has resulted in several seconds of delay before analysis of the next sample. When sampling rates on the order of several samples per minute are desired, this delay may substantially reduce the rate at which samples may be processed.

Several techniques may be used to cool the gas chromatography columns at sufficient rates. In general, these techniques include either blowing relatively cold air over the column or thermally coupling the column to another element that is either cold to begin with, or can be cooled very quickly.

One technique uses liquid nitrogen as the cooling mechanism. Liquid nitrogen is significantly colder than ambient air, which leads to a very large temperature difference and extremely fast cooling. Liquid nitrogen can be used by blowing the very cold nitrogen boiling off of the liquid over the column to be cooled and using simple baffles to turn the flow of cold nitrogen on and off. Liquid nitrogen also may be used by pumping the liquid nitrogen through a cold block, similar to the aluminum cold block discussed above with respect to FIG. 9. When using liquid nitrogen, care must be taken prevent water condensation from interfering with operation of the system.

Another technique relies on adiabatic cooling, which is the cooling of a gas that results from expansion of the gas. Adiabatic cooling may be achieved by using a bottle of gas, or a compressor and compressed air, and allowing the pressurized gas to expand in a controlled manner.

As discussed above with respect to FIG. 9, Peltier coolers may be used to cool the gas chromatography column. A thin coating of insulating material may be used to prevent a thermal "short" between the column and the aluminum block or other thermal mass cooled by the Peltier coolers. There is a tradeoff between the thickness of the insulating material, the recovery time, and the power required to heat the column. Reducing the thickness of the insulation decreases the recovery time, but increases the power that must be applied to the column to overcome heat loss to the aluminum block when the column is being heated. In general, the practicality of using Peltier coolers increases when the column is a short column such as is employed in a vapor concentrator, because a short column may be mounted easily in a cold block that is cooled by a Peltier cooler. While gas chromatography columns used for sample analysis also could be cooled by mounting them in a cold block, a more complicated cold block would be required because these columns typically are longer and wound in a helical manner.

One technique to using Peltier coolers to cool a gas chromatography column is to include radiative fins in an isolated oven that contains the gas chromatography column. These fins are then cooled using Peltier coolers. When cooling of the column is desired, a circulating fan is activated to expose the column to air cooled by the Peltier coolers. The circulating fan is turned off when the column is being heated.

The cooling rate for a given analysis may be determined based on the cooling capacity of the cold block (i.e., the cooling capacity of the Peltier coolers) and the temperature difference between the cold block and the column being cooled. Accordingly, the number of samples that can be analyzed in a given amount of time is directly proportional to the cooling capacity of the Peltier coolers.

Similar results can be achieved using a standard refrigeration system with a freon-type coolant. However, Peltier coolers are simpler and tend to be more reliable. These types of cooling systems are most effective when the column or vapor concentrator needs to be cooled to a temperature below the ambient temperature.

Water also may be used as a coolant, and may be combined with antifreeze when cooling below the freezing temperature of water is desired. For example, water or an antifreeze solution may be cooled using a refrigeration system and then pumped through or around the components to be cooled.

When ambient temperatures or temperatures slightly above ambient are desired, air convection may be used to cool the column. For example, an air convection technique is discussed above with respect to FIG. 1. In another technique, direct air cooling of the column or vapor concentrator may be replaced by air cooling of fins attached to a large cold block made from aluminum or another material.

Temperature Measurement and Control

Figure 17:
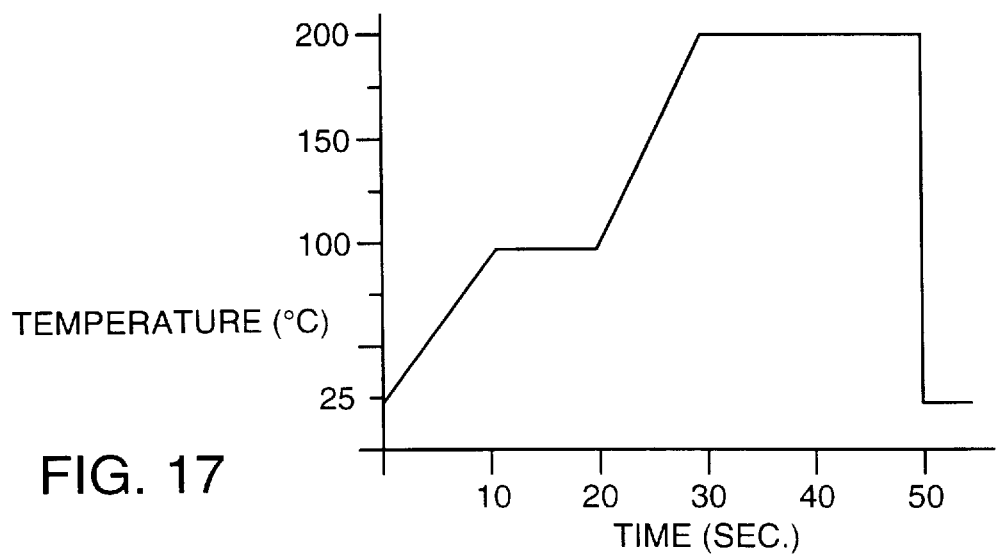
FIG. 17 is a graph of a temperature versus time.

Regardless of the techniques used to heat or cool the gas chromatography column, the system must be able to measure and to control the temperature of the gas chromatography column accurately, precisely and quickly for effective, high-speed analysis of samples. As disclosed in U.S. Pat. No. 5,268,302, which is incorporated herein by reference, the gas chromatography column may need to be at different temperatures during various portions of the analysis. For example, a representative profile of desired temperature variation with time is shown in FIG. 17.

The temperature of the gas chromatography column may be varied by controlling the electrical current supplied to the resistive tubing of the column. In prior gas chromatography systems, exemplified by U.S. Pat. Nos. 5,108,705 and 5,300,758, which are incorporated herein by reference, temperature programming was accomplished by proportional control of the voltage applied to the column. An increase in applied voltage resulted in an increase in the current flowing through the metal sheath of the column and a corresponding increase in the temperature of the column. When full power was not required (as when the column was being maintained at a temperature plateau) power was dissipated through a control transistor. Settings in the system had to be changed from time to time to compensate for any changes in the sheath resistance, as when installing a different gas chromatography column for a different analysis, where a replacement column differed in length, wall thickness, or diameter due to production variations.

Figure 18:
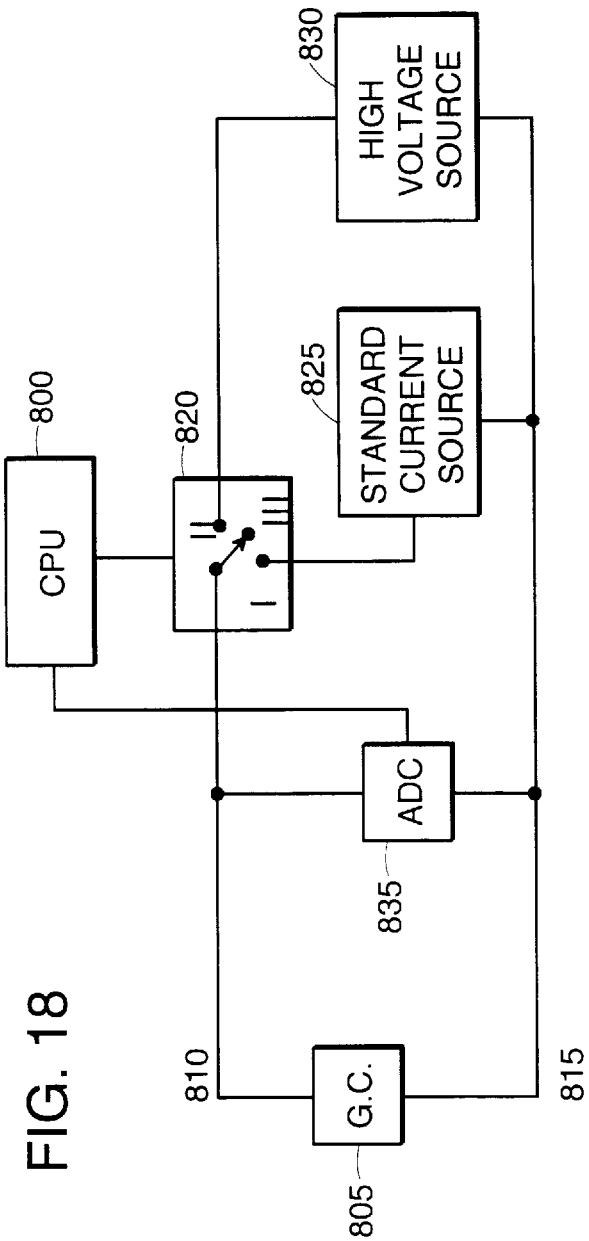
FIG. 18 is a block diagram of a system for controlling the temperature of a gas chromatograph column.

Referring to FIG. 18, the present approach uses a process 800 to continually check the resistance of the gas chromatography column. The resistance of the metal sheath is a function of its temperature, and may be expressed, for example, as:

$$R = R_o(1 + K(T - T_o))$$

where R is the resistance at temperature T, $R_o$ is the fixed base resistance (e.g. at ambient or base temperature $T_o$) and K is the temperature coefficient of resistance for the sheath material, which is a known constant value for the particular material. From this, it follows that temperature (T) is a linear function of resistance (R) which may be expressed as:

$$T = T_o + K'(R - R_o),$$

where K' is also a constant. Hence the change in temperature from base or ambient value (i.e., $T - T_o$) is a linear function of the change in resistance (i.e., $R - R_o$). Accordingly, the column's resistance may be taken as a representation of the column's temperature once the column's resistance at a base or ambient temperature is determined.

The profile of FIG. 17 shows the desired temperature at each instant during the gas chromatography analysis period. The microprocessor 800 readily determines the current time during the analysis period by counting the clock pulses or cycles of the microprocessor's clock oscillator from the beginning of the analysis period. Since the desired temperature at each instance along the profile is known, the desired resistance at each instance may be determined using the desired temperature, the known starting resistance and temperature, and the resistivity coefficient. The resistance values may be stored in a data table by the microprocessor, or may be computed when needed by interpolation between the known slope-change points of the temperature profile.

Figure 19:
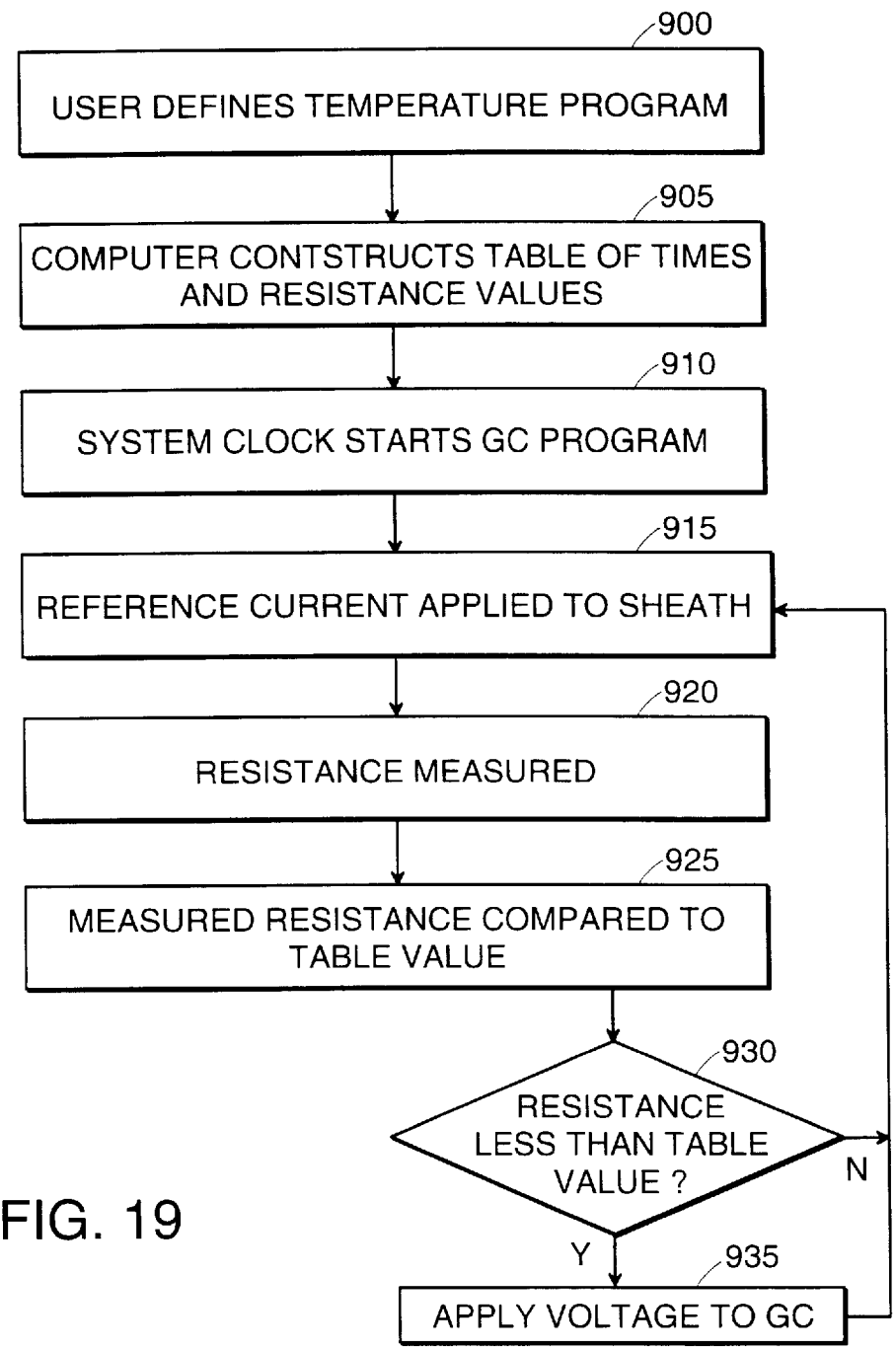
FIG. 19 is a flow chart of a procedure implemented by the system of FIG. 18.

The functioning of the system and its software is shown in the flow chart of FIG. 19. Initially, the user defines a desired profile of temperature versus time and supplied the profile to the processor 800 (step 900), either in table form or as a statement of temperature variation. For example, a typical temperature profile for a vapor concentrator may raise the temperature from a starting or ambient value to 250° C. as quickly as possible and then maintain that temperature for two seconds. For the gas chromatography column, a typical temperature profile may be as shown in FIG. 17, in which the temperature is raised from the starting temperature to 100° C. in ten seconds, maintained at 100° C. for ten seconds, increased from 100° C. to 200° C. in the next ten seconds, maintained at 200° C. for the next twenty seconds, and then returned to the starting temperature as rapidly as possible.

The processor 800 stores or converts the user-supplied data for desired temperature versus time into a table of desired resistance versus time (step 905). Where resistance varies uniformly with time, the value at various time instants may be calculated by interpolation instead of being stored as a table. The processor generates this data using the base column resistance at a known temperature and the temperature coefficient of resistivity for the column. The processor determines the base resistance by measuring the column resistance while passing air having a known temperature measured over the column.

The processor controls the temperature in successive control intervals or cycles. The processor initiates the gas chromatography temperature profile upon injection of the sample into the gas chromatography column from the vapor concentrator as discussed above (step 910) and counts off clock pulses to determine the successive control intervals. Each control interval may be from about 1–10 milliseconds in duration. At each control interval, the processor measures the column resistance and, if necessary, adjusts the column temperature. In particular, the processor applies a reference current to the sheath (step 915) to measure the resistance of the sheath (step 920), and then compares the resistance to the stored table value for that control interval (step 925).

If the measured resistance is less than the desired value (step 930), the processor applies a voltage to the sheath (step 935). Otherwise, the processor does not apply a voltage to the sheath. The system then repeats the cycle during the next control interval by repeating the step of applying a reference current to the sheath (step 915) and the steps that follow.

Figure 20:
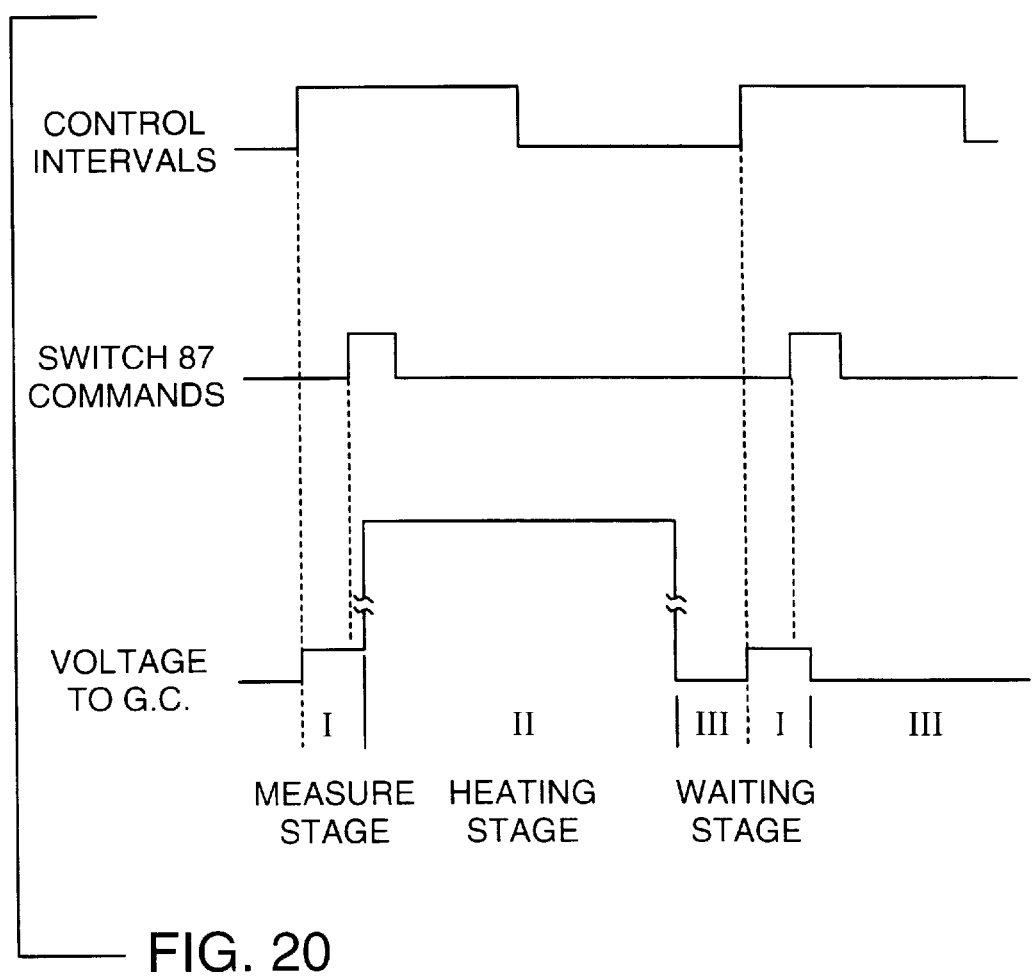
FIG. 20 is a timing diagram for the system of FIG. 18.

As shown in the timing diagram of FIG. 20, each control interval has three successive stages: a measuring stage I, a heating stage II, and a waiting stage III. During the measuring stage I, the processor measures the actual sheath resistance by applying a small voltage to the metal sheath and compares the actual resistance with the desired resistance. If the measured resistance is below the desired resistance, this indicates that the column temperature is below the desired (profile) temperature. The processor responds to this condition by applying a heating voltage to the metal sheath during the heating stage II. This voltage may be of a fixed duration that is less than or equal to the control interval.

The duration of the heating stage, and of the control interval, are chosen based on the heat capacity of the gas chromatography column and the desired accuracy of temperature control. By way of illustration, if temperature control accuracy of 0.1° C. is desired, then the temperature of the gas chromatography column must not rise more than 0.1° C. in any single control cycle, because temperature measurements are made only once in each control cycle. Thus, in this example, if the heating voltage is able to raise the temperature of the gas chromatography column at a maximum rate of 20° C. per second, then the duration of the heating power must be limited to a fixed duration of 5 milliseconds or less. During the remainder of the control interval, no voltage is applied to the column. Accordingly, this stage of the control interval is designated as a waiting stage III.

For a typical six-meter long gas chromatography column, the resistance at ambient temperature is about 12.8 ohms. A heating voltage of 90 volts will produce a temperature rise in excess of 10° C. per second. Accordingly, applying the heating voltage of 90 volts for one millisecond will produce a temperature rise of approximately 0.01° C. In the case of a vapor concentrator, a typical starting resistance is 0.50 ohms, and a heating voltage of 24 volts will produce a temperature rise of 4° C. in one millisecond.

By using a short control interval, the processor 800 is able to control the temperature of the gas chromatography column or the vapor concentrator in accordance with the desired profile. Since the control intervals occur very rapidly, each for a duration of one to a few milliseconds, the effect is to attain the desired temperature very rapidly and to maintain the temperature essentially at the desired value until a change is required.

As shown in FIG. 18, the gas chromatography column 805 includes electrical terminals 810 and 815 at the ends of the column's metal sheath so that a voltage applied across the terminals produces an electric current in the sheath that heats the column to the desired temperature. The terminal 810 is connected to a first terminal of a power switch 820 that is controlled by the processor 800. In a first position, the switch 820 connects a current source 825 between the terminals 810 and 815. The current source 825 produces a small measurement current of, for example, 100 mA. In a second position, the switch 820 connects a fixed voltage source 830 between the terminals 810 and 815. The voltage source 830 produces a large voltage (e.g., about 90 volts for the column 805 or 24 volts for a vapor concentrator) that serves to heat the column. In a third position, the switch is open so that no voltage is applied to the column.

An analog-to-digital convertor (ADC) 835 measures the voltage between the terminals 810 and 815 and provides a digital signal indicative of the voltage to the processor 800. When the standard current (e.g., 100 milliamperes) is applied to the sheath, the voltage indicated by the ADC 835 represents the resistance of the sheath. For example, if the ADC indicates one volt for a current of 100 milliamperes, the resistance would be 10 ohms. This voltage is applied in digital form to the processor. As pointed out above, this voltage represents the measured sheath resistance at each control interval.

The processor compares the resistance value provided by the ADC 835 with the corresponding desired resistance. If the desired resistance is determined to be higher than the measured resistance, which indicates that the column temperature is lower than desired, the processor controls the switch to connect the high voltage source 830 to the column for a predetermined fixed duration. This provides extra heating energy to the load to increase its temperature and hence its resistance. At the end of that duration, the processor changes the switch to the open position (III) for the remainder of the control interval. In the next control interval, the processor reconnects the standard current source to the load and measures the resistance. If the resistance and the temperature are below the desired values, then the processor connects the voltage source 830 to the column. These cycles are repeated at a high rate (e.g., about once every one to ten milliseconds) until the processor determines that the measured resistance is at least equal to the desired resistance. When that condition exists, the processor places the switch 820 in the open position (III) for that control interval. This pattern of measurement followed by waiting continues until the measurement in a control interval indicates that the temperature must be increased. At that point, the processor 800 again connects the voltage source 830 to the column for a fixed duration.

The control scheme may be further refined to permit finer control of the temperature. The method of FIG. 19 uses on/off temperature control (i.e., during the power period, the heating power is either entirely on for a fixed duration or entirely off). Finer control can be obtained by proportional control, or by more sophisticated control schemes known as proportional-integral (PI) or proportional-integral-differential (PID) control.

In these techniques, the heating power is varied according to the size of the error signal, i.e., the difference between the actual temperature and the desired temperature. This may be done by varying either the heating voltage, as was done in U.S. Pat. No. 5,300,758, or by varying the duration of the power period. Processor-based devices that implement PID by such time-proportioning are well known in process control. An example is Omega model CN4400, which is available from Omega Engineering of Stamford, Conn. Algorithms for PID control are described in Perry's Chemical Engineer's Handbook, Sixth Edition, pages 22–77, McGraw-Hill, New York 1984, at for example, equations 22–30 on pages 22–77. These algorithms are incorporated herein by reference.

Figure 21:
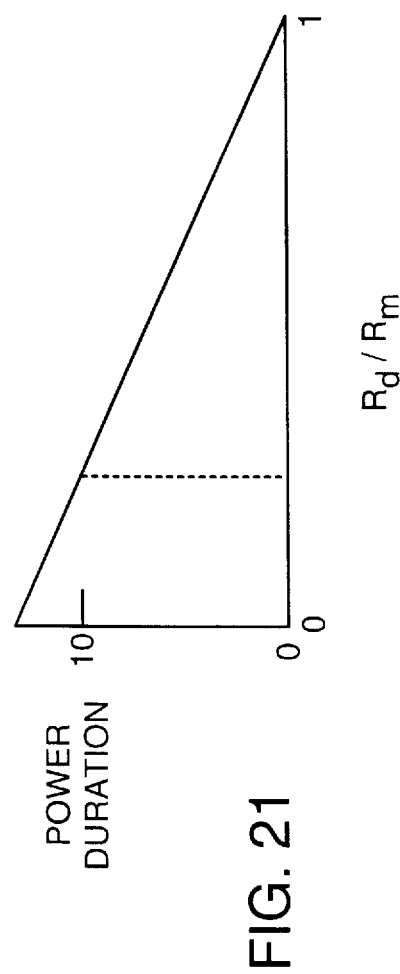
FIG. 21 is a graph of a relationship between resistance ratios and power duration.

As shown in FIG. 21, the duration of the heating period may be controlled based on the relationship between the measured resistance ($R_m$) and the desired resistance ($R_d$) to achieve time-proportional PID control. By the PID algorithms, the computer calculates the required voltage duration during each control interval. The circuit of FIG. 18 operates as discussed above, with the exception that the processor 800 disconnects the voltage source 830 after the heating stage has had a desired duration, instead of after a fixed period as described above. This provides a pulse-duration variation analogous to pulse width modulation (PWM).

In this way, the temperature of the column is measured repetitively, and power is supplied as necessary cause the system to closely follow the desired temperature profile, such as shown in FIG. 17, until the profile calls for a rapid decrease in temperature, as at the end of the analysis cycle.

The approach described above permits ready substitution of one column for another, without requiring recalibration and automatically takes into account any difference in the resistance of the column sheath which the replacement column may have. When measurement at base (e.g. ambient) conditions for the substituted column determines that $R_o$ has changed for the base temperature, the processor recomputes each of the resistance values stored in its memory to derive a new modified resistance table for the system to follow for the substituted column. This may be achieved easily, since each R value in the stored table should be adjusted by the same amount in response to a change in $R_o$ to keep the same profile.

By virtue of this arrangement, it is no longer necessary to recalibrate the system upon replacement of a column by a new column which may have a different length or base resistance. The base resistance of the replacement column is automatically determined and the table of desired resistance at each control interval instant is recomputed for the new column resistance values stored, by reducing each resistance value by the difference between the previous and new base resistances without requiring other recalibration.

The desired temperature profile is then closely followed for the new column during the control intervals as described above. Thus, the column may be structured as a readily replaceable module, where desired, without requiring manual re-calibration upon replacement.

The gas chromatography column may need to be heated to different temperatures and to rapidly transition from one temperature to another. Temperature control may need to be highly precise over wide temperature ranges.

As discussed above, one technique to measuring the temperature of the gas chromatography column is to measure the electrical resistance of a metal sheath surrounding the column when the current used for heating the column is not applied. A known relationship between the resistance and the temperature may permit temperature measurement with precision on the order of 0.5° C. and absolute accuracy of ±2° C. within a wide temperature range from 25° C. to 400° C. This resistance measurement technique may work well when a control cycle is divided into a measurement portion in which the temperature is measured and a heating portion in which the metal sheath is heated by application of an electric current. A MOSFET transistor or similar control element may be used so that heating energy is not consumed during the measurement portion of the cycle. This method facilitates the design of economical, compact, and simple systems for controlling, measuring and rapidly changing the temperature of a gas chromatography column or a vapor concentrator.

Other techniques also may be used to measure the sheath temperature. For example, the temperature may be measured using a radiation pyrometer or a distributed thermocouple. A distributed thermocouple uses coaxial wires made from different metals and surrounding the gas chromatography column. Different combinations of materials in the distributed temperature sensors can provide more sensitive and accurate sensors for specific temperature ranges. Pyrometers provide electrical and thermal isolation.

Techniques for providing controlled heating of the column include the application of width modulated pulses of energy to the column and ON/OFF control of the application of heating energy with short temperature measurement intervals facilitating up to 98% duty cycles. Rapidly switching between measurement and control enables the system to achieve a highly accurate temperature profile by reducing the duration of the control cycle, which can be as short as 100 microseconds.

An arrangement for heating and cooling a gas chromatography column 1000 is illustrated in FIGS. 22 and 23. As previously noted, the column may be an internally coated quartz capillary tube threaded inside a very small (e.g., 0.02 inch diameter) metal needle-stock tube, as described in more detail in U.S. Pat. No. 5,300,758 (which is incorporated herein by reference) at col. 5, lines 44–66.

The column 520 is coiled into a helix and placed within an annular casing 1005 that includes a cylindrical outer wall 1010 and a cylindrical inner wall 1015 that together define an annular space 1020. The coiled column 1000 has an inlet 1025 and an outlet 1030. The upper end of the annular casing 1005 is coupled to an exhaust duct 1035. Air from a centrifugal blower 1040 or other similar source is supplied to an inlet duct 1045 to force cooling air into the annular space 1020 that contains the column 1000. Air may also be passed through an inner passage 1050 defined by the inner wall 1015. An annular cover or damper 1055 covers the inlet to the annular space 1020 and is controlled by a solenoid 1060. In the absence of excitation of the solenoid, the damper 1055 is kept in an open position, either under the influence of gravity or by a suitable spring. Upon energization of the solenoid 1060, the damper 1055 closes and prevents air from flowing into the annular space 1020, while having little, if any, effect on air flowing within the inner passage 1050.

The damper 1055 is kept closed during the portion of the operating cycle of the gas chromatography system in which the column 1000 is being heated and the chromatograph is being produced. At the end of this portion of the operating cycle, the column is rapidly cooled by turning off the mechanism (e.g., the electric current) used to heat the column and by opening the damper to permit cooling air through the annular space 1020. The resulting forced air convection rapidly returns the column 1000 to the column's initial cool state. Air flow for cooling the gas chromatography column 1000 enters through an inlet at the back of the gas chromatography system, passes through the duct system under the influence of the centrifugal blower 1040, and is returned to an outlet at the back of the instrument.

A similar arrangement may be used to control the temperature of a vapor concentrator 515 (or multiple vapor concentrators). The concentrator may be enclosed in its own housing, with forced air provided for cooling. A damper may be used to cut off air flow abruptly upon attaining a desired low temperature. The damper is controlled as described above.

In some arrangements, a common casing may be used for the gas chromatography column and the concentrator or concentrators, so that a single blower and damper control arrangement serves to cool both the gas chromatography column and the concentrator. If a single blower is used, individual dampers may be provided for each device, so that the devices may be cooled independently at different times, with some devices being heated while others are being cooled. Alternatively, individual casings and dampers may be used to control the air for the individual concentrators.

For some applications, such as detecting permanent gases and light hydrocarbons, it is desirable to operate the gas chromatography column 1000 at temperatures as low as 15° C. and the vapor concentrator at temperatures as low as −10° C. For these applications, the air provided to the annular space 1020 may be passed through a refrigerated heat exchanger (not shown) to cool the air to subambient temperatures. Use of a refrigerated heat exchanger or a similar device may be particularly important in industrial process control applications in which the ambient temperature may be as high as 40° C.

Temperature Gradients

Figure 24:
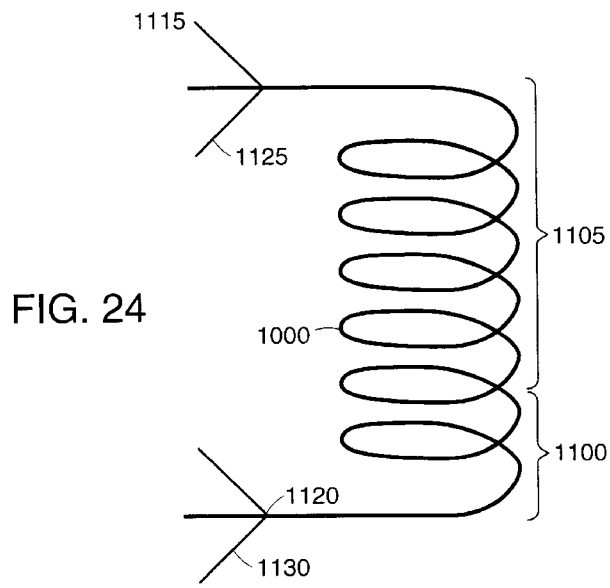
FIG. 24 is a schematic view of a vertically-oriented gas chromatography column which may be subject to thermal gradients.

The annular geometry facilitates rapid cooldown. This geometry is also relatively compact, which is an advantage for the packaging design of an instrument that includes the column 1000. However, as shown in FIG. 24, undesirable temperature gradients may arise from this geometry. In particular, the two helical coils 1100 at the bottom tend to be significantly cooler than the other coils 1105 of the column 1000. This has been observed experimentally both by using thermocouples and by inspecting the gas chromatography column for darkening due to heat exposure.

The temperature gradient arises from convective air currents that result in a so-called chimney effect. There is an asymmetry between the very lowest turns of the helix 1100 and all successive turns. Air that is heated by the lowest coils of the helix rises and creates a warmer environment for the coils immediately above. As the heated air rises, the heated air loses heat to the walls of the chamber in which the column 1000 is housed. This may result in a steady state condition in which the local temperature is independent of the vertical position, except for at the very lowest turns of the helix, which are not heated from below.

It is noted that the two lowest coils 1100, rather than just the single lowest coil, are different from the other coils. One simple explanation for this is that the vertical distance needed to achieve a steady state temperature as a result of cooling by the annular walls is greater than the vertical height of one turn of the helix.

Figure 25:
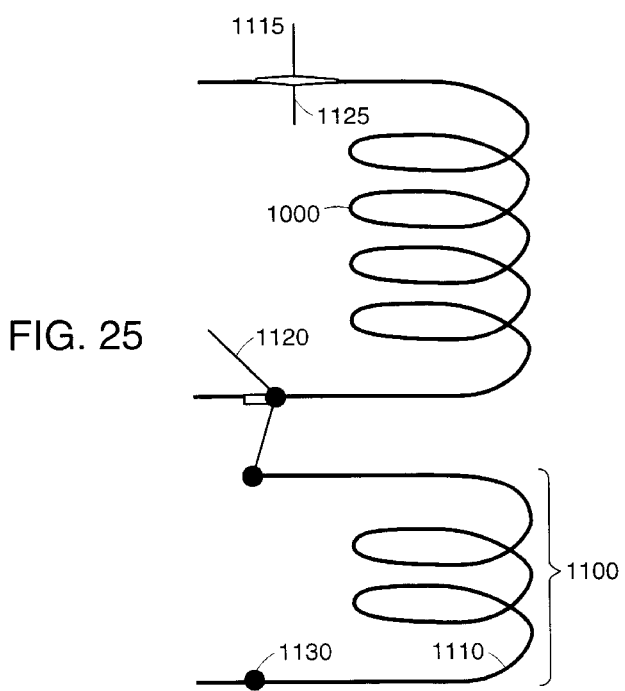
FIG. 25 is a schematic view of a vertically-oriented gas chromatography column, with structure to reduce thermal gradients.

FIG. 25 shows an alternative configuration in which a short decoy column 1110 is mounted immediately below the analytical gas chromatography column. The decoy column 1110 includes a metal capillary identical to that of the column 1000 and has helical geometry and spacing identical to that of the column 1000, but is not connected to the gas flow of the column 1000. The decoy column 1110 acts as the lowest coils 1100 of the helix to avoid having an undesirable thermal gradient in the column 1000. Electrically, temperature sensing leads 1115 and 1120 are applied across the column 1000, while the electric heating current flows in series through both the column 1000 and the decoy column 1100 from a first lead 1125 to a second lead 1130.

Figure 26:
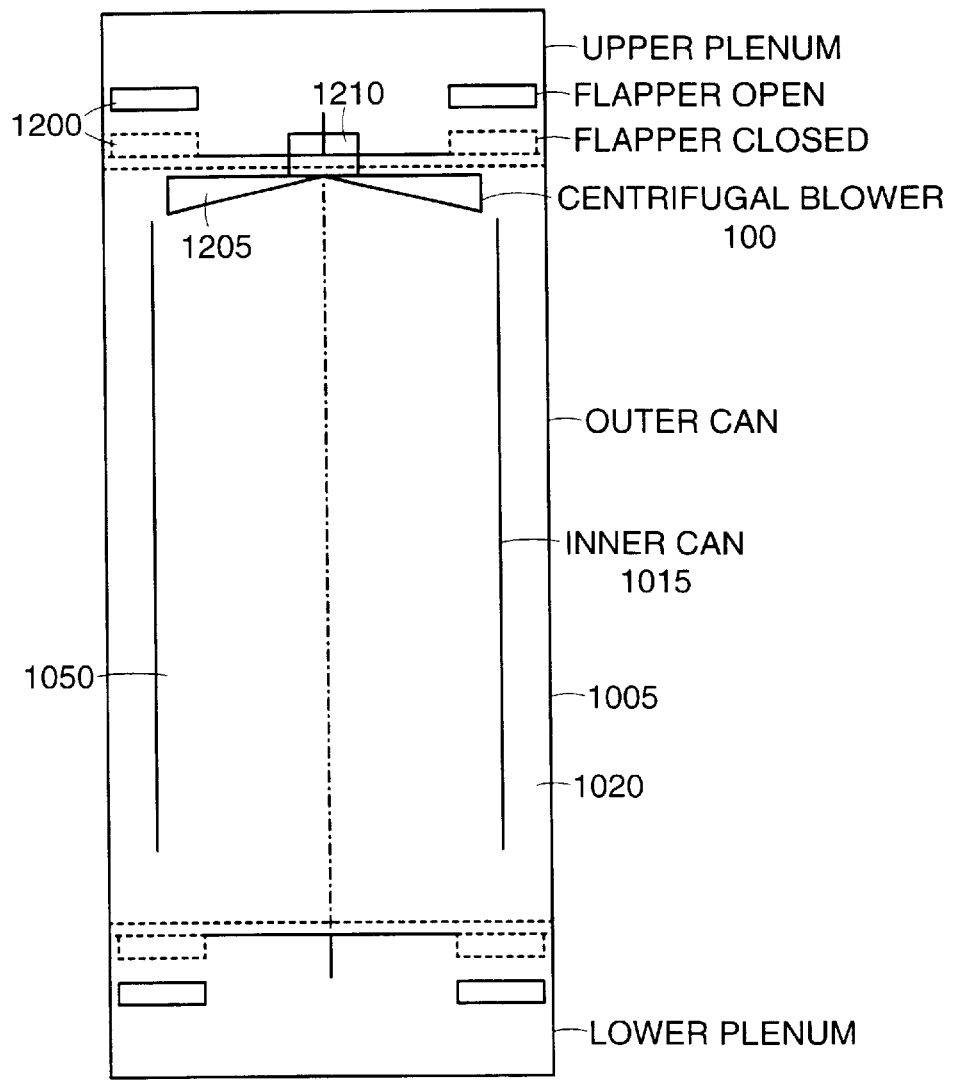
FIG. 26 is a cross-sectional view of a vertically-oriented gas chromatography column with a fan or blower to minimize thermal gradients.

FIG. 26 illustrates an alternative technique for preventing gradients, in which several features have been added relative to the configuration of FIG. 22. First, the inner wall 1015 has been shortened by about 0.25" at the top and 0.25" at the bottom to interconnect the air spaces 1020 and 1050 at both the top and bottom. Second, a damper mechanism 1200 is added at the top of the casing 1005 so that the air space of the casing 1005 can be isolated from the air space of the exhaust duct during the gas chromatography analysis. Third, a fan or blower 1205 is installed to create a closed loop air flow between the spaces 1020 and 1050. The speed of the air flow is selected by controlling the voltage to the drive motor 1210 of the fan, and the direction of air flow is selected by the choice of impeller type for the fan 1205 and the placement of the fan 1205 within the casing 605. For example, fans having centrifugal impellers may be placed at the top or bottom of the casing while an axial fan may be placed in the middle of the space 1050. The closed loop air flow mixes the air and eliminates or reduces the vertical thermal gradient.

Another problem associated with vertical thermal gradients is that, due to temperature differences resulting from the thermal gradient, the top coils will have a higher resistance than the lower coils and will consequently heat at a higher rate than the rate at which the bottom coils heat.

The use of a fan as discussed above eliminates or reduces the vertical thermal gradient by forcing the column to be thermally homogenous. Another technique to eliminating or reducing the thermal gradient is to isolate the entire length of the column.

One way to isolate the length of the column is to spread the column over a large area and leave large distances between all parts of the column. This prevents thermal crosstalk between different parts of the column. The problem with this technique is that it would require considerable space and may be impractical for that reason.

Another way of isolating the length of the column is to place the column in a vacuum. This would eliminate heat transfer due to convection. However, considerable difficulties may be associated with sealing the system and cooling the column after each analysis.

Another way to isolate the column is to put the column into a thermally insulating sleeve. For example, the sleeve could be made from glass fiber, a polymer like Teflon, or any other coating material that provides thermal insulation and will not break down as a result of the high temperatures to which the column is heated. With an insulating sleeve, each section of the column would be heated independently of the other section. Another benefit to this technique would include reduced heat loss and a resulting reduction in power consumption. If tubular insulation were used instead of placing the column in a metal sheath, the column could run parallel with a heating wire placed in the insulating tube. In general, the heating wire would have a higher resistance than the metal sheath and, for this reason, would be easier to control. A problem associated with thermally insulating the column and the heating element is a resulting increase in the time required to cool the column. Another problem would be an inability to reverse divergence of the temperature of the column when the temperature is being ramped.

As noted above, the temperature of the column may be made homogenous by using a fan to mix the air inside the space 1020. With this technique, the casing 1005 should be sealed and all surfaces should be insulated to minimize heat loss. Vigorous stirring of the air ensures that there are no temperature gradients and that the entire column begins at the same temperature and stays the same as the temperature is ramped. A problem associated with this technique is that more power is required to heat the column because a relatively large volume of air must be heated along with the column.

In some instances, thermal gradients along the length of the gas chromatography column are desirable. In particular, higher resolution gas chromatographic separations may be achieved by providing a varying temperature along the length of the column. For example, a continuously varying temperature starting at a high temperature at the injection end of the column and ending at a lower temperature at the detection end of the column may be useful in enhancing the resolution of certain samples. Techniques for achieving temperature variations along a gas chromatography column are discussed below.

Figure 27A:
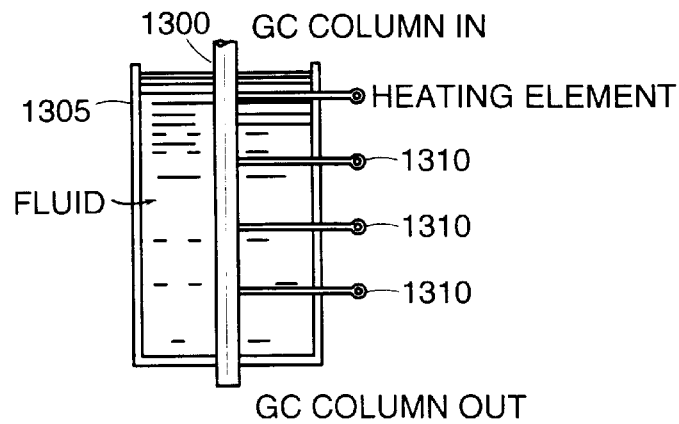
FIGS. 27A–27F are diagrams of gas chromatography columns with structure for introducing thermal gradients along the length of the column.

In a first technique, as illustrated in FIG. 27A, a column 1300 is suspended vertically in a container 1305 of liquid or gas that is heated from the top of the container. A smooth thermal gradient should be achieved, but may be difficult to control. Temperature sensors 1310 may be installed along the length of the column to measure the operating temperature at any point. Oil or air may be suitable working fluids for typical gas chromatography temperatures.

Figure 27B:
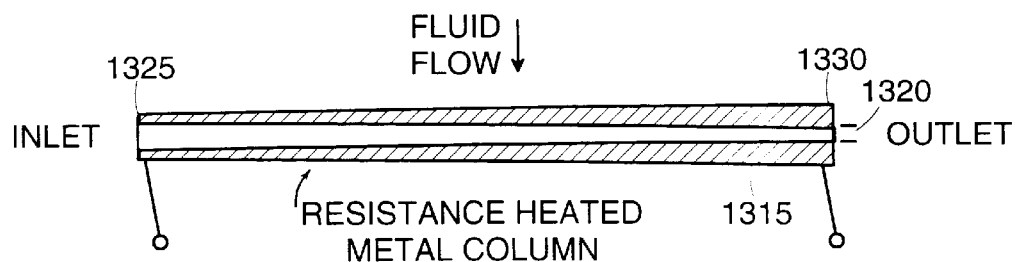

In a second technique, as illustrated in FIG. 27B, a resistance-heated metal tube 1315 serves as the gas chromatography column. The inner diameter 1320 of the column is constant along the length of the column. The outer diameter of the column increases at a constant rate from the inlet 1325 to the outlet 1330, which results in an increasing cross-section, decreasing resistance, and decreasing power dissipation along the length of the column from the inlet to the outlet. The column is mounted in a chamber in which a circulating fluid, such as air, removes heat from the column at a fairly uniform rate, and is heated using a low voltage, high current power supply.

The temperature profile can be tailored by adjusting the rate at which the cross-sectional area varies along the column. For instance, a linear change, resulting in a conical column, would result in a square-law temperature profile. A desired degree of change along the length can be achieved by controlling the change in the cross-section along the length. The operating temperature at any point, but not the profile, can be changed by adjusting the electrical current supplied to the column.

Figure 27C:
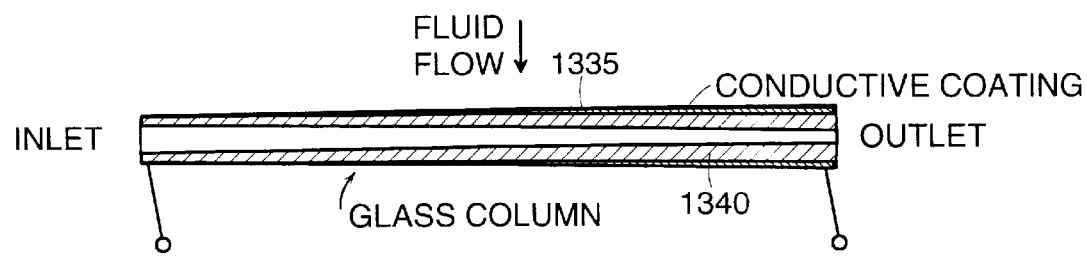

In a third technique, as illustrated in FIG. 27C, a variable conductivity coating 1335 is applied to a glass column 1340. In particular, the coating is evaporated or plated onto the column to achieve a variable watt density along the length of the column. This technique has a potential advantage over the technique illustrated in FIG. 27B in that it may be less expensive to produce a column having a variable resistance coating than to produce an accurate profile in metal tubing. Once again, it is assumed that heat is carried away from the column at a fairly uniform rate in order to achieve the desired temperature profile.

Figure 27D:
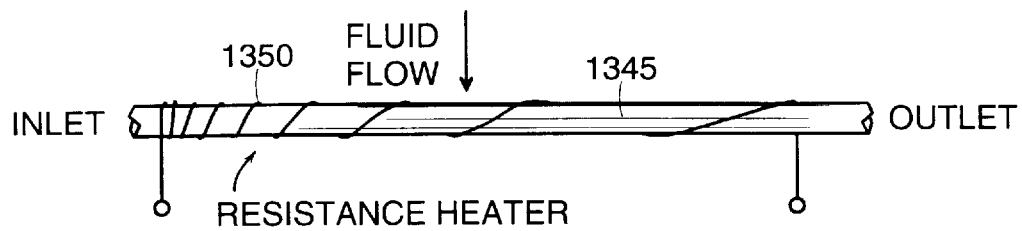

In a fourth technique, as illustrated in FIG. 27D, a metal or glass column 1345 of constant cross section is used along with an external electrical heater that produces variable watt density along the length of the column. The variable electric heater may be produced, for example, by winding wire 1350 around the column in a spiral having a pitch that varies along the length of the column. A potential disadvantage of this technique is that the spiral temperature profile might be translated to the inside of the column to produce a series of hot and cold spots along the length of the column. Using current manufacturing techniques, a column wrapped with wire in a varying-pitch spiral would be relatively expensive to manufacture. This is an important consideration since the column must be considered to be a consumable or disposable item.

Figure 27E:
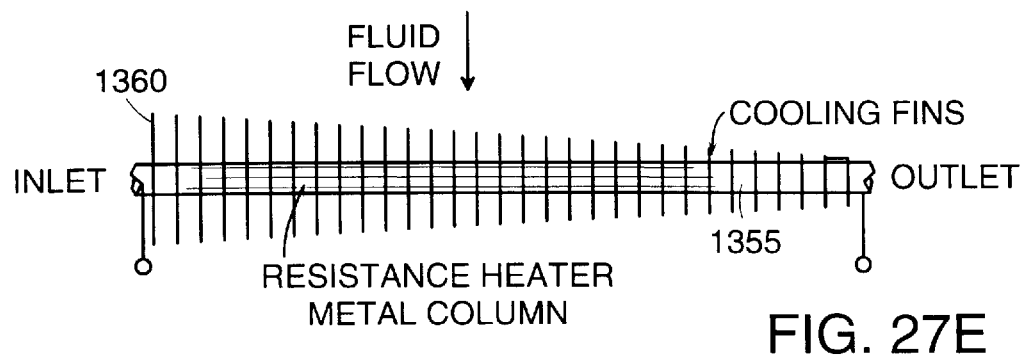

In a fifth technique, as illustrated in FIG. 27E, heat is removed from a uniformly heated column at different rates along the length of the column. For example, annular cooling fins 1355 of varying diameter may be installed along the length of a metal tube 1360 having constant cross section and heated by electrical resistance, and a fluid may be circulated around the tube to remove heat from the tube. The amount of heat carried away from different portions of the tube will vary with the sizes of the fins attached to the different portions of the tube, which will result in a variable temperature profile along the length of the tube.

Figure 27F:
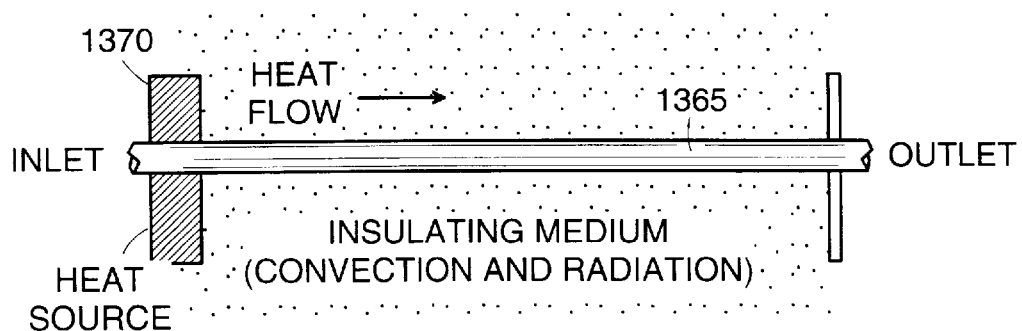

In a sixth technique, as illustrated in FIG. 27F, a thermal gradient is achieved along a column 1365 by adding heat at one end of the column using a heat source 1370 and extracting heat from the other end of the column. This technique requires significant insulation of the column. For example, a metal column installed in a vacuum might achieve this effect. It would be difficult to build a column of the required length in this manner without using a highly conductive metal.

Flow Control

Another important consideration is flow control within the system. In a chromatography system, the relative stability of the flow of carrier gas between analyses has a significant impact on whether the results generated by the system are reproducible. Accordingly, a gas chromatography system must be able to consistently control the flow of carrier gas. Moreover, some analyses require variations in the carrier gas flow. For these analyses, the system must be able to produce consistent variable flows.

Flow control may be particularly important during temperature programming. Since the density of the carrier gas changes as a function of temperature, the flow through a particular flow restrictor will continually vary with the varying temperatures associated with temperature programming. The system may add another dimension of control by providing the ability to control and vary the carrier gas flow. The flow may be controlled using a mass flow controller. A less expensive method is to use a series of flow restrictors such as capillaries or similar devices and a series of associated solenoid valves that permit selective activation of different flow restrictors or combinations thereof to vary the flow through the system.

Other flow control issues also are relevant. For example, as noted above, it has been found that back flushing the vapor concentrators (i.e., reversing the flow through the vapor concentrators before desorbing contaminants from the vapor concentrators) leads to quicker chromatography. The use of back-flushed vapor concentrators also permits the use of stacked vapor concentrators (i.e., vapor concentrators arranged in series) with a first vapor concentrator being optimized for materials having relatively low volatility and the second vapor concentrator being optimized for materials having high volatility.

Sound waves may be used to measure flows through the system. If a sound transmitter positioned at one end of a pipe produces a sound that is detected by a sound receiver at the other end of the pipe, the sound received by the receiver will have the same frequency as the sound produced by the transmitter when there is no gas flow through the pipe. When there is gas flow, then the frequency received will differ from the frequency transmitted as a function of the gas flow and other easily measured factors. This effect could be used to measure the gas flow within the gas chromatography column. Note that the frequency used has to be such that the corresponding wavelength is small compared to the diameter of the column.

The Sample Extractor

A sample may be obtained by wiping surfaces believed to contain sample material, or by blowing air upon such surfaces to dislodge substances to be analyzed, and thereafter collecting a sample for examination from the object used to wipe the surface or from the blown air. However, such methods may not be suitable for sensitive examination of granular or particulate materials that are carrying or coated with undesirable substances. For example, the wiping technique may be unsuitable for detecting pesticides on wheat kernels or other grains.

Figure 28:
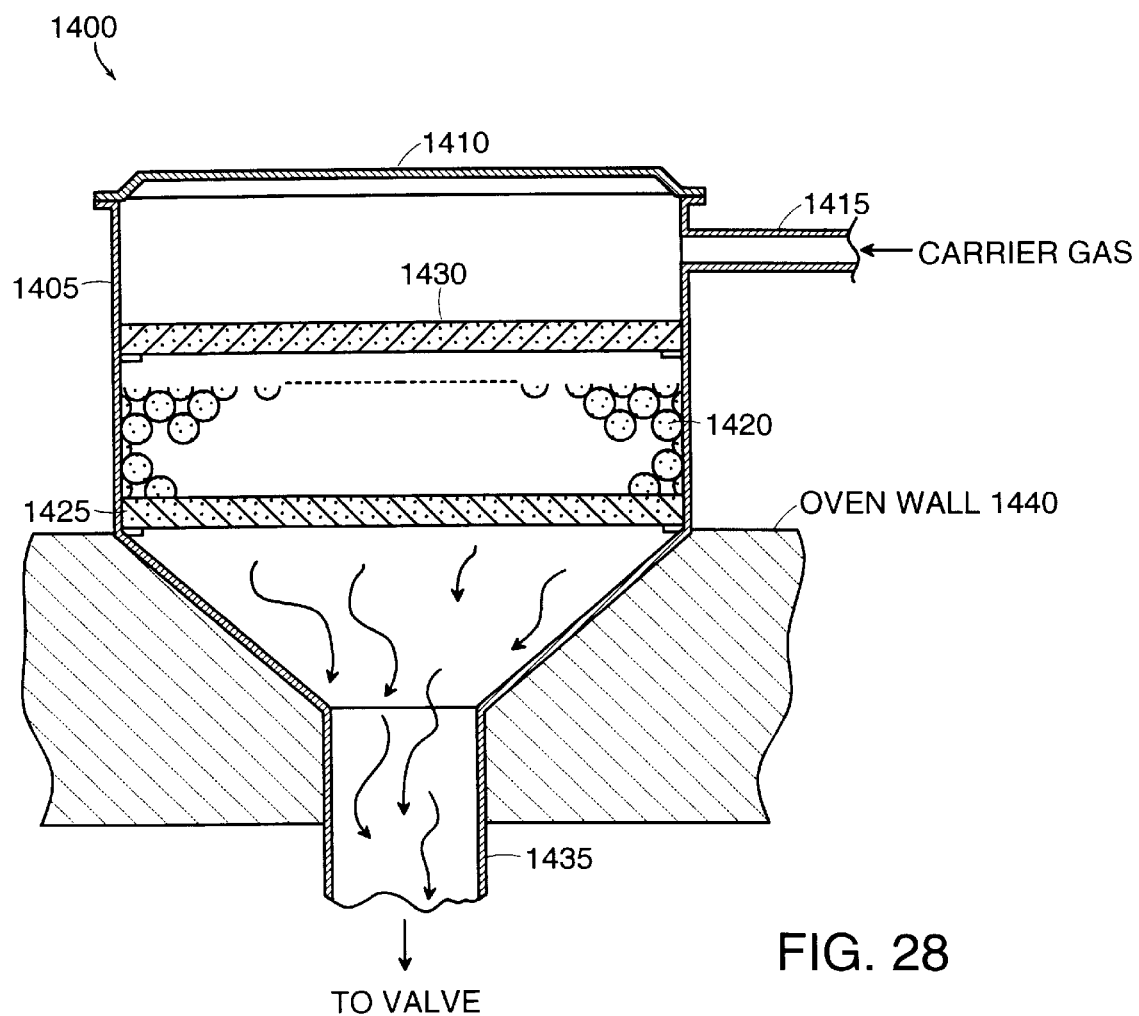
FIG. 28 is a cross-sectional view of a sample extraction module.

FIG. 28 shows a schematic elevation cross-section of a sample extraction module 1400 that may be used as the sample extractor 510 of the system of FIG. 15. The sample extraction module 1400 constitutes an improvement over previous "head-space analysis" and solvent extraction methods that were used for analysis of granular or particulate materials. In head-space analysis, a collected sample is placed in the bottom of a vessel and a stream of carrier gas is passed over the sample. The transport of the vapor components out of the solid sample and into the carrier gas stream occurs by passive diffusion, which is a slow process. By contrast, the present method forces heated carrier gas through a bed of granular solid material so that the heated gas is placed in intimate contact with the various surfaces of the granular material, and extraction of volatile components and dislodging of adhered substances is both rapid and reproducible, leading to typical sample extraction times ranging from 10 seconds to several minutes depending on the nature of the sample. By contrast, head-space techniques typically require one hour or more for sample collection.

Similarly, previous solvent extraction techniques typically required several hours to obtain a sample and also required expensive disposal of waste solvents. The extractor of the present invention is particularly adapted to extract impurities such as pesticides coating granular products such as wheat kernels or other grains or granular materials.

The extractor module includes a funnel-shaped housing 1405, of dimensions appropriate to the size of sample desired. The housing 1405 is capable of being sealed as by a cover 1410, and has an inlet 1415 for receiving carrier gas. The granular material 1420 to be analyzed is placed within the funnel 1405 on a screen or filter 1425. A diffuser 1430 may be placed on top of the material 1420 to distribute the carrier gas. The exit 1435 from the funnel 1405 passes through the wall 1440 of an oven that contains valves and other components of the gas chromatography system.

The funnel 1405 and the cover 1410 are electrically heated to between 100° C. and 300° C. After adding granular material 1420 and sealing the cover 1410 to the funnel body 1405, heated carrier gas or air (at a temperature of about 150° C.–300° C.) is passed through the granular material and into the oven.

Volatile components which may be coated on or included with the sample material 1420 are liberated from the sample material and enter the carrier gas stream that is passed into the system for processing and analysis.

The Detector

In a conventional gas chromatography system, the volume of the detector plays as important role in determining the sensitivity and resolution of the analysis. Standard detectors may recognize gas chromatography peaks that are approximately 0.5 seconds wide or wider. However, high speed gas chromatography systems, such as the system of the invention, generate peaks that are less than 0.1 seconds wide. If two adjacent peaks that were each 0.1 seconds wide and were separated by 0.2 seconds (resolution=2), were detected by a conventional detector, the peaks would both occupy the detector cell at the same time and the resolution would be compromised.

The effective volume of a detector may be reduced (and the resolution may be increased) by operating the detector under vacuum. For example, when a flame ionization detector is operated under vacuum, the hydrogen flame will elongate and the ionization chemistry that occurs at different flame temperatures can be distinguished by using multiple collectors. Responses specific to the analyte functional groups can be used to improve selectivity and sensitivity of the analysis.

Other embodiments are within the scope of the following claims.

What is claimed is:

1. A flash chromatography module, including:

a coiled sheath;

a gas chromatography column positioned within and separate from the sheath, wherein a layer of gas chromatography material is located on an inner surface of the column, and an outer diameter of the column is smaller than an inner diameter of the sheath; and connectors positioned at ends of the sheath;

wherein cross sections of the connectors are substantially larger than cross sections of the sheath so that the connectors provide rigid structures for mechanically connecting the flash chromatography module to a gas chromatography system.

2. The flash chromatography module of claim 1, wherein the coiled sheath comprises an electrically conductive sheath configured to be rapidly heated by application of an electrical current.

3. The flash chromatography module of claim 2, wherein the connectors comprise electrical connectors configured to provide a current path for applying the electrical current to the conductive sheath.

4. The flash chromatography module of claim 2, wherein the coiled sheath comprises a metal sheath.

5. The flash chromatography module of claim 4, further comprising:

a thin layer of electrical insulation on an outer surface of the metal sheath; and a thin layer of metal on the electrical insulation;

wherein the thin layer of metal is configured for use in measuring a temperature of the metal sheath.

6. The flash chromatography module of claim 2, further comprising a layer of electrically insulative material positioned around an exterior surface of the sheath.

7. The flash chromatography module of claim 6, wherein the layer of insulative material comprises a woven glass sleeve.

8. The flash chromatography module of claim 1, wherein a difference between the outer diameter of the column and the inner diameter of the sheath is small enough to permit rapid heat transfer from the sheath to the column.

9. The flash chromatography module of claim 1, further comprising a holder configured to maintain the sheath in the coiled configuration.

10. The flash chromatography module of claim 9, wherein the holder comprises a set of side rails having grooves that are each sized to receive a coil of the sheath.

11. The flash chromatography module of claim 10, wherein the side rails are made from electrically insulative material.

12. A high speed gas chromatography system including the flash chromatography module of claim 1, the system further comprising a heated, controlled-temperature region, wherein the flash chromatography module is positioned external to the controlled-temperature region.

13. The system of claim 12, wherein the controlled-temperature region includes a pair of fittings configured to receive the connectors of the flash chromatography module.

14. The system of claim 13, wherein the fittings and the connectors serve as heat sinks to prevent excessive heating of the layer of gas chromatography material in regions adjacent to the connectors.

15. The system of claim 13, wherein the controlled-temperature region comprises a chamber and wherein the fittings are positioned in an insulated wall of the chamber.

16. The system of claim 15, wherein each fitting includes a first portion positioned within the chamber and a second portion that extends through the wall.

17. The system of claim 15, further comprising electrical leads secured to the fittings.

18. The system of claim 17, wherein the electrical leads comprise a first pair of electrical leads secured to the fittings to establish a circuit by which an electrical current may be applied to the sheath to heat the sheath and the column.

19. The system of claim 18, wherein the electrical leads further comprise a second pair of electrical leads secured to the fittings to establish a circuit for measuring an electrical resistance of the sheath to measure the temperature of the sheath and the column.

20. The system of claim 15, further comprising an enclosure containing the flash chromatography module, wherein the insulated wall of the chamber thermally isolates the enclosure from the chamber.

21. The system of claim 13, further comprising a current source configured to apply an electrical current between the fittings for heating the sheath of the flash chromatography module.

22. The system of claim 21, further comprising a processor connected to the current source and configured to control the time and duration at which the current source applies the electrical current between the fittings for heating the sheath of the flash chromatography module.

23. The system of claim 12, further comprising an enclosure containing the flash chromatography module and configured to isolate the flash chromatography module from external temperature effects.

24. The system of claim 23, further comprising an air-circulating fan positioned within the enclosure, the fan being operable to control temperature gradients within the enclosure as a result of heating of the sheath.

25. The system of claim 24, wherein the fan is configured to be turned on or off.

26. The system of claim 24, wherein the fan comprises a variable-speed fan.

27. The system of claim 23, further comprising a controllably-opened air flow path configured to permit cooling air to enter the enclosure.

28. The system of claim 27, wherein the air flow path comprises louvers configured to be opened to permit cooling air to enter the enclosure.

29. The system of claim 23, further comprising a source of liquid nitrogen for use in cooling the enclosure.

30. The system of claim 23, further comprising a source of pressurized gas, wherein the system is configured to use the pressurized gas in cooling the enclosure through adiabatic cooling.

31. The system of claim 23, further comprising a Peltier cooler operable to cool the enclosure.

32. The system of claim 23, further comprising a refrigeration system for use in cooling the enclosure.

33. The system of claim 23, wherein the enclosure further comprises a movable panel configured to permit selective access to an interior of the enclosure.

34. The system of claim 23, wherein the enclosure comprises an annular casing having a cylindrical outer wall and a cylindrical inner wall that together define an annular space in which the flash chromatography module is positioned.

35. The system of claim 34, wherein the enclosure further comprises an inlet duct configured to permit cooling air to enter the annular space to cool the flash chromatography column.

36. The system of claim 35, further comprising a movable damper configured to selectively open or close the inlet duct.

37. The system of claim 12, further comprising a detector and a flow path between the detector and the gas chromatography module, wherein at least a portion of the flow path is positioned in the controlled-temperature region.

38. The system of claim 12, further comprising an enclosure external to the controlled-temperature region, wherein the flash chromatography module is positioned in the enclosure.

39. The system of claim 38, wherein the enclosure is configured to isolate the flash chromatography module from heat sources external to the enclosure.

40. The system of claim 39, wherein the flash chromatography module is the only heat source internal to the enclosure.

41. The system of claim 39, wherein the sheath comprises a conductive metal sheath, the system further comprising circuitry for supplying an electrical current to the sheath for heating the gas chromatography material.

42. The system of claim 39, further comprising an insulating wall between the enclosure and the controlled-temperature region, the insulating wall providing an abrupt temperature transition between the enclosure and the controlled-temperature region.

43. The system of claim 38, wherein the flash chromatography module is the only heat source internal to the enclosure.

44. The system of claim 38, wherein the enclosure includes an interior surface having a low thermal mass.

45. The system of claim 38, further comprising an air-circulating fan positioned in the enclosure and being operable to control temperature gradients within the enclosure.

46. The system of claim 38, further comprising:
an inlet configured to operate in an open position that permits flow into the enclosure through the inlet or a closed position that prevents flow into the enclosure through the inlet, and
a control mechanism attached to the inlet and operable to switch the inlet between the open and closed positions.

47. The system of claim 46, further comprising a processor configured to control the system, the processor being connected to the control mechanism and configured to cause the control mechanism to place the inlet in the open position to cool the flash chromatography module.

48. The system of claim 12, further comprising a vapor concentrator connected to the controlled-temperature region.

49. The system of claim 48, wherein the controlled-temperature region comprises a controlled-temperature chamber and wherein the vapor concentrator is positioned in a wall of the controlled-temperature chamber.

50. The system of claim 48, wherein the vapor concentrator comprises:
a short gas chromatography column,
a metal sheath surrounding the column, and
circuitry for applying an electrical current to the sheath to rapidly heat the column.

51. The system of claim 50, wherein the vapor concentrator further comprises a large thermal mass surrounding the sheath for rapidly cooling the column and the sheath when the circuitry does not apply an electrical current to the sheath.

52. The system of claim 51, wherein the large thermal mass of the vapor concentrator comprises a block of metal.

53. The system of claim 52, wherein the large thermal mass of the vapor concentrator comprises a block of aluminum.

54. The system of claim 51, wherein the vapor concentrator further comprises a Peltier cooler connected to the large thermal mass and configured to cool the thermal mass.

55. The system of claim 51, wherein the vapor concentrator further comprises a source of liquid nitrogen for use in cooling the large thermal mass.

56. The system of claim 51, wherein the vapor concentrator further comprises a source of pressurized gas for use in cooling the large thermal mass through adiabatic cooling.

57. The system of claim 51, wherein the vapor concentrator further comprises a refrigeration system for use in cooling the large thermal mass.

58. The system of claim 12, further comprising a second flash chromatography module including:
a coiled sheath;
a gas chromatography column positioned within and separate from the sheath, wherein a layer of gas chromatography material is located on an inner surface of the column, and an outer diameter of the column is smaller than an inner diameter of the sheath; and
connectors positioned at ends of the sheath;
wherein cross sections of the connectors are substantially larger than cross sections of the sheath so that the connectors provide rigid structures for mechanically connecting the second flash chromatography module to the gas chromatography system, and
the second flash chromatography module is positioned external to the controlled-temperature region.

59. The system of claim 58, further comprising an enclosure containing the first and second flash chromatography modules, the enclosure being thermally isolated from the temperature-controlled region.

60. The system of claim 58, further comprising a first enclosure containing the first flash chromatography module and a second enclosure containing the second flash chromatography module, wherein the enclosure are thermally isolated from the temperature-controlled region.

61. The system of claim 12, further comprising control circuitry configured to measure an electrical resistance between ends of the coiled sheath to determine a temperature of the coiled sheath and further configured to apply an electrical current between ends of the coiled sheath to heat the coiled sheath.

62. The system of claim 61, wherein the control circuitry comprises a processor.

63. The system of claim 62, wherein the processor is configured to control the temperature of the coiled sheath to conform to a desired temperature profile by:
measuring the electrical resistance between ends of the coiled sheath,
determining the temperature of the coiled sheath based on the measured resistance, and
adjusting the electrical current applied between ends of the coiled sheath to adjust for any difference between the determined temperature and a corresponding component of the desired temperature profile.

64. The system of claim 63, wherein the processor is configured to repeat the measuring, determining and adjusting steps.

65. The flash chromatography module of claim 1, further comprising a decoy column positioned below the coiled sheath, the decoy column including:
a second coiled sheath; and
a second layer of gas chromatography material within the second coiled sheath;
wherein the second coiled sheath is disconnected from the coiled sheath of the flash chromatography module so that gas flowing through the coiled sheath of the flash chromatography module does not flow through the second coiled sheath.

66. A high speed gas chromatography system including the flash chromatography module of claim 65, wherein a first end of the first coiled sheath is electrically connected to a first end of the second coiled sheath, the system further comprising:
circuitry for measuring an electrical resistance between the first end of the first coiled sheath and a second end of the first coiled sheath to determine a temperature of the first coiled sheath; and
circuitry for applying an electrical current between the second end of the first coiled sheath and a second end of the second coiled sheath to heat the coiled sheaths.

67. A high speed gas chromatography system, comprising:
a gas chromatography module, including:
a coiled sheath;
a gas chromatography column positioned within and separate from the sheath, wherein a layer of gas chromatography material is located on an inner surface of the column, and an outer diameter of the column is smaller than an inner diameter of the sheath; and
connectors positioned at ends of the sheath;
wherein cross sections of the connectors are substantially larger than cross sections of the sheath so that the connectors provide rigid structures for mechanically connecting the chromatography module to a gas chromatography system;

a heated, controlled-temperature region, an enclosure external to the controlled-temperature region and containing the chromatography module, and an insulating wall between the controlled-temperature region and the enclosure, the insulating wall providing an abrupt temperature transition between the enclosure and the controlled-temperature region.

68. The system of claim 67, wherein the insulating wall includes an insertion path configured to permit insertion of a portion of the gas chromatography column from the enclosure into the controlled-temperature chamber.

69. The system of claim 68, further comprising a fitting positioned in the insulating wall and configured to provide the insertion path.

70. The system of claim 69, wherein the fitting is configured to act as a heat sink to remove excess heat from a portion of the gas chromatography column positioned in the insertion path.

71. The system of claim 69, wherein the fitting is configured to provide an electrical current to the connector.

72. The system of claim 67, further comprising an air-circulating fan positioned in the enclosure and being operable to control temperature gradients within the enclosure.

73. The system of claim 67, wherein the coiled sheath comprises an electrically conductive sheath configured to be rapidly heated by application of an electrical current.

74. The system of claim 73, wherein the connectors comprise electrical connectors configured to provide a current path for applying the electrical current to the conductive sheath.

75. The system of claim 67, wherein the enclosure is configured to isolate the chromatography module from heat sources external to the enclosure.

76. The system of claim 75, wherein the chromatography module is the only heat source internal to the enclosure.

77. The system of claim 75, wherein the enclosure includes an interior surface having a low thermal mass.

78. The system of claim 67, further comprising control circuitry configured to measure an electrical resistance between ends of the coiled sheath to determine a temperature of the coiled sheath and further configured to apply an electrical current between ends of the coiled sheath to heat the coiled sheath.

79. The system of claim 78, wherein the control circuitry comprises a processor.

80. The system of claim 79, wherein the processor is configured to control the temperature of the coiled sheath to conform to a desired temperature profile by:

measuring the electrical resistance between ends of the coiled sheath, determining the temperature of the coiled sheath based on the measured resistance, and adjusting the electrical current applied between ends of the coiled sheath to adjust for any difference between the determined temperature and a corresponding component of the desired temperature profile.

81. The system of claim 67, wherein the insulating wall includes a pair of fittings configured to receive the connectors of the chromatography module.

82. The system of claim 81, wherein the fittings and the connectors serve as heat sinks to prevent excessive heating of the layer of gas chromatography material in regions adjacent to the connectors.

83. The system of claim 81, further comprising a current source configured to apply an electrical current between the fittings for heating a sheath of the gas chromatography column.

84. The system of claim 83, further comprising a processor connected to the current source and configured to control the time and duration at which the current source applies the electrical current between the fittings for heating the sheath of the chromatography module.

85. The system of claim 67, further comprising an air-circulating fan positioned within the enclosure, the fan being operable to control temperature gradients within the enclosure.

86. The system of claim 67, further comprising a controllably-opened air flow path configured to permit cooling air to enter the enclosure.

87. The system of claim 86, wherein the air flow path comprises louvers configured to be opened to permit cooling air to enter the enclosure.

88. The system of claim 67, wherein the enclosure further comprises a movable panel configured to permit selective access to an interior of the enclosure.

89. The system of claim 67, further comprising a vapor concentrator connected to the controlled-temperature region.

90. The system of claim 89, wherein the controlled-temperature region comprises a controlled-temperature chamber and wherein the vapor concentrator is positioned in a wall of the controlled-temperature chamber.

91. The system of claim 89, wherein the vapor concentrator comprises:

a short gas chromatography column, a metal sheath surrounding the column, and circuitry for applying an electrical current to the sheath to rapidly heat the column.

92. The system of claim 91, wherein the vapor concentrator further comprises a large thermal mass surrounding the sheath for rapidly cooling the column and the sheath when the circuitry does not apply an electrical current to the sheath.

93. The system of claim 92, wherein the large thermal mass of the vapor concentrator comprises a block of metal.

94. The system of claim 93, wherein the large thermal mass of the vapor concentrator comprises a block of aluminum.

95. The system of claim 92, wherein the vapor concentrator further comprises a Peltier cooler connected to the large thermal mass and configured to cool the thermal mass.

96. The system of claim 67, further comprising:

a wire threaded through the sheath and along the column; and circuitry configured to measure a resistance of the wire as a measure of a temperature of the column.

97. The system of claim 67, further comprising a thermocouple positioned within the sheath for measuring a temperature of the column.

98. The system of claim 67, further comprising:

a valve positioned within the controlled-temperature region;

wherein ends of the gas chromatography column extend through the insulating wall and are connected to the valve.

99. The system of claim 98, wherein the valve comprises a high-speed, multi-port, two-way valve.

100. The system of claim 99, further comprising a processor configured to control operation of the valve.

101. The system of claim 67, wherein an interior of the enclosure comprises a relatively thin layer of metal overlying a relatively thick layer of insulation to provide the enclosure with a low thermal mass.

102. The system of claim 67, further comprising:
a second gas chromatography column.

103. The system of claim 102, wherein the second gas chromatography column is positioned within the enclosure.

104. The system of claim 102, further comprising a second enclosure external to the controlled-temperature region and configured to receive a gas chromatography column, wherein the second gas chromatography column is positioned within the second enclosure.

105. The system of claim 102, wherein the system is configured to permit independent temperature programming of the gas chromatography columns.

106. The system of claim 105, wherein the system is configured to heat the columns at heating rates in a range from 1° C. per second to 100° C. per second.

107. The system of claim 67, further comprising an infrared energy source configured to direct infrared energy at the chromatography module.

108. The system of claim 107, wherein the sheath is coated with a material that absorbs a wavelength of infrared energy emitted by the infrared energy source.

109. The system of claim 67, further comprising a microwave energy source configured to direct microwave energy at the sheath.

110. The system of claim 109, wherein the sheath is coated with a material that absorbs microwave energy emitted by the microwave energy source.

111. The system of claim 110, wherein the material comprises a metal film.

112. The system of claim 67, further comprising a coil positioned around the module and configured to direct high frequency radio energy at the module.

* * * * *